(12) United States Patent
Johnson

(10) Patent No.: US 7,820,678 B2
(45) Date of Patent: Oct. 26, 2010

(54) SODIUM CHANNEL BLOCKERS

(75) Inventor: Michael R. Johnson, Durham, NC (US)

(73) Assignee: Parion Sciences, Inc., Durham, NC (US)

(*) Notice: Subject to any disclaimer, the term of this patent is extended or adjusted under 35 U.S.C. 154(b) by 364 days.

(21) Appl. No.: 11/950,674

(22) Filed: Dec. 5, 2007

(65) Prior Publication Data
US 2008/0076782 A1 Mar. 27, 2008

Related U.S. Application Data

(60) Division of application No. 11/261,734, filed on Oct. 31, 2005, now Pat. No. 7,345,044, which is a continuation of application No. 10/973,474, filed on Oct. 27, 2004, now Pat. No. 7,026,325, which is a division of application No. 10/367,947, filed on Feb. 19, 2003, now Pat. No. 6,903,105.

(51) Int. Cl.
*A61K 31/4965* (2006.01)
(52) U.S. Cl. .............................. 514/255.06; 514/255.05
(58) Field of Classification Search .................. None
See application file for complete search history.

(56) References Cited

U.S. PATENT DOCUMENTS

| | | | |
|---|---|---|---|
| 6,858,614 B2 | 2/2005 | Johnson | |
| 6,858,615 B2 | 2/2005 | Johnson | |
| 6,903,105 B2 * | 6/2005 | Johnson | 514/255.06 |
| 6,995,160 B2 | 2/2006 | Johnson | |
| 7,026,325 B2 * | 4/2006 | Johnson | 514/255.05 |
| 7,030,117 B2 | 4/2006 | Johnson | |
| 7,064,129 B2 | 6/2006 | Johnson et al. | |
| 7,186,833 B2 | 3/2007 | Johnson | |
| 7,189,719 B2 | 3/2007 | Johnson | |
| 7,192,958 B2 | 3/2007 | Johnson | |
| 7,192,959 B2 | 3/2007 | Johnson | |
| 7,192,960 B2 | 3/2007 | Johnson | |
| 7,241,766 B2 | 7/2007 | Johnson | |
| 7,247,636 B2 | 7/2007 | Johnson | |
| 7,247,637 B2 | 7/2007 | Johnson et al. | |
| 7,317,013 B2 | 1/2008 | Johnson | |
| 7,345,044 B2 * | 3/2008 | Johnson | 514/255.06 |
| 2004/0198747 A1 | 10/2004 | Johnson | |
| 2004/0198749 A1 | 10/2004 | Johnson | |
| 2005/0080092 A1 | 4/2005 | Johnson | |
| 2005/0080093 A1 | 4/2005 | Johnson et al. | |
| 2005/0090505 A1 | 4/2005 | Johnson et al. | |
| 2005/0228182 A1 | 10/2005 | Johnson et al. | |
| 2006/0040954 A1 | 2/2006 | Johnson | |
| 2006/0052394 A1 | 3/2006 | Johnson et al. | |
| 2006/0052395 A1 | 3/2006 | Johnson et al. | |
| 2006/0063780 A1 | 3/2006 | Johnson | |
| 2006/0142306 A1 | 6/2006 | Johnson | |
| 2006/0142581 A1 | 6/2006 | Johnson | |
| 2006/0205738 A1 | 9/2006 | Johnson et al. | |
| 2007/0032509 A1 | 2/2007 | Johnson et al. | |
| 2007/0265280 A1 | 11/2007 | Johnson | |

OTHER PUBLICATIONS

Dorwald F. A. Side Reactions in Organic Synthesis, 2005, Wiley: VCH, Weinheim p. IX of Preface.*
U.S. Appl. No. 12/249,175, filed Oct. 10, 2008, Boucher et al.
U.S. Appl. No. 12/304,006, Dec. 9, 2008, Johnson et al.
U.S. Appl. No. 12/304,042, Dec. 9, 2008, Johnson.
U.S. Appl. No. 12/304,040, Dec. 9, 2008, Johnson.
U.S. Appl. No. 10/920,527, filed Aug. 18, 2004, Hopkins.
U.S. Appl. No. 11/573,693, filed Feb. 14, 2007, Johnson.
U.S. Appl. No. 11/573,413, filed Feb. 8, 2007, Johnson.
U.S. Appl. No. 11/573,421, filed Feb. 8, 2007, Johnson.
U.S. Appl. No. 11/696,003, filed Apr. 3, 2007, Johnson.
U.S. Appl. No. 11/852,003, filed Sep. 7, 2007, Johnson et al.
U.S. Appl. No. 11/851,803, filed Sep. 7, 2007, Johnson et al.
U.S. Appl. No. 11/960,989, filed Dec. 20, 2007, Johnson et al.
U.S. Appl. No. 11/835,902, filed Aug. 8, 2007, Johnson et al.
U.S. Appl. No. 12/049,946, filed Mar. 17, 2008, Johnson et al.
U.S. Appl. No. 12/049,968, filed Mar. 17, 2008, Johnson et al.
U.S. Appl. No. 12/049,894, filed Mar. 17, 2008, Johnson et al.
U.S. Appl. No. 12/050,010, filed Mar. 17, 2008, Johnson.
U.S. Appl. No. 12/049,993, Mar. 17, 2008, Johnson.
U.S. Appl. No. 12/050,019, Mar. 17, 2008, Johnson.
U.S. Appl. No. 12/061,837, filed Apr. 3, 2008, Johnson et al.
U.S. Appl. No. 12/061,864, filed Apr. 3, 2008, Johnson et al.
U.S. Appl. No. 12/098,581, filed Apr. 7, 2008, Johnson.
U.S. Appl. No. 60/495,725, filed Aug. 18, 2003, Johnson.
U.S. Appl. No. 60/495,720, filed Aug. 18, 2003, Johnson.
U.S. Appl. No. 60/495,712, filed Aug. 18, 2003, Johnson.
U.S. Appl. No. 60/602,312, filed Aug. 18, 2004, Johnson.
U.S. Appl. No. 60/602,327, filed Aug. 18, 2004, Johnson.
U.S. Appl. No. 60/812,091, filed Jun. 9, 2006, Johnson.
U.S. Appl. No. 60/812,077, filed Jun. 9, 2006, Johnson et al.
U.S. Appl. No. 60/812,078, filed Jun. 9, 2006, Johnson.
U.S. Appl. No. 60/842,669, filed Sep. 7, 2006, Johnson et al.
U.S. Appl. No. 60/842,963, filed Sep. 8, 2006, Johnson et al.
U.S. Appl. No. 60/845,171, filed Sep. 18, 2006, Johnson et al.
U.S. Appl. No. 60/909,818, filed Apr. 3, 2007, Johnson et al.
U.S. Appl. No. 60/978,887, filed Oct. 10, 2007, Boucher et al.
U.S. Appl. No. 60/978,874, filed Oct. 10, 2007, Boucher et al.
U.S. Appl. No. 60/987,663, filed Nov. 13, 2007, Johnson et al.
U.S. Appl. No. 61/013,387, filed Dec. 13, 2007, Johnson et al.
U.S. Appl. No. 61/030,313, filed Feb. 21, 2008, Johnson.
U.S. Appl. No. 61/031,466, filed Feb. 26, 2008, Johnson.
U.S. Appl. No. 12/171,814, filed Jul 11, 2008, Johnson et al.
U.S. Appl. No. 12/171,867, filed Jul. 11, 2008, Johnson et al.
U.S. Appl. No. 12/171,897, filed Jul. 11, 2008, Johnson et al.
U.S. Appl. No. 12/190,022, filed Aug. 12, 2008, Johnson.
U.S. Appl. No. 61/079,989, filed Jul. 11, 2008, Boucher et al.
U.S. Appl. No. 12/179,353, filed Jul. 24, 2008, Johnson.

* cited by examiner

*Primary Examiner*—James O Wilson
*Assistant Examiner*—Jeffrey H Murray

(57) ABSTRACT

Provided are methods of increasing hydration of mucosal surfaces by topically administering sodium channel blocking pyrazinoylguanidine compounds.

12 Claims, No Drawings

SODIUM CHANNEL BLOCKERS

CONTINUING APPLICATION DATA

This application is a Divisional of U.S. application Ser. No. 11/261,734, now allowed, filed on Oct. 31, 2005, which is a Continuation of U.S. application Ser. No. 10/973,474, filed on Oct. 27, 2004, now U.S. Pat. No. 7,026,325, which is a Divisional of U.S. application Ser. No. 10/367,947, filed on Feb. 19, 2003, now U.S. Pat. No. 6,903,105.

BACKGROUND OF THE INVENTION

1. Field of the Invention

The present invention relates to sodium channel blockers. The present invention also includes a variety of methods, of treatment using these inventive sodium channel blockers.

2. Description of the Background

The mucosal surfaces at the interface between the environment and the body have evolved a number of "innate defense", i.e., protective mechanisms. A principal form of such innate defense is to cleanse these surfaces with liquid. Typically, the quantity of the liquid layer on a mucosal surface reflects the balance between epithelial liquid secretion, often reflecting anion ($Cl^-$ and/or $HCO_3^-$) secretion coupled with water (and a cation counter-ion), and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channel and liquid absorption. The epithelial protein that mediates the rate-limiting step of $Na^+$ and liquid absorption is the epithelial $Na^+$ channel (ENaC). ENaC is positioned on the apical surface of the epithelium, i.e. the mucosal surface-environmental interface. Therefore, to inhibit ENaC mediated $Na^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers designed to exhibit the increased potency, reduced mucosal absorption, and slow dissociation ("unbinding" or detachment) from ENaC required for therapy of these diseases.

Chronic bronchitis (CB), including the most common lethal genetic form of chronic bronchitis, cystic fibrosis (CF), are diseases that reflect the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health effectively removes from the lung potentially noxious toxins and pathogens. Recent data indicate that the initiating problem, i.e., the "basic defect," in both CB and CF is the failure to clear mucus from airway surfaces. The failure to clear mucus reflects an imbalance between the amount of liquid and mucin on airway surfaces. This "airway surface liquid" (ASL) is primarily composed of salt and water in proportions similar to plasma (i.e., isotonic). Mucin macromolecules organize into a well defined "mucus layer" which normally traps inhaled bacteria and is transported out of the lung via the actions of cilia which beat in a watery, low viscosity solution termed the "periciliary liquid" (PCL). In the disease state, there is an imbalance in the quantities of mucus as ASL on airway surfaces. This results in a relative reduction in ASL which leads to mucus concentration, reduction in the lubricant activity of the PCL, and a failure to clear mucus via ciliary activity to the mouth. The reduction in mechanical clearance of mucus from the lung leads to chronic bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the syndromes of CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, β-agonists, inhaled steroids, anti-cholinergic agents, and oral theophyllines and phosphodiesterase inhibitors are all in development. However, none of these drugs treat effectively the fundamental problem of the failure to clear mucus from the lung. Similarly, in cystic fibrosis, the same spectrum of pharmacologic agents is used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics ("TOBI") designed to augment the lungs' own killing mechanisms to rid the adherent mucus plaques of bacteria. A general principle of the body is that if the initiating lesion is not treated, in this case mucus retention/obstruction, bacterial infections became chronic and increasingly refractory to antimicrobial therapy. Thus, a major unmet therapeutic need for both CB and CF lung diseases is an effective means of re-hydrating airway mucus (i.e., restoring/expanding the volume of the ASL) and promoting its clearance, with bacteria, from the lung.

R. C. Boucher, in U.S. Pat. No. 6,264,975, describes the use of pyrazinoylguanidine sodium channel blockers for hydrating mucosal surfaces. These compounds, typified by the well-known diuretics amiloride, benzamil, and phenamil, are effective. However, these compounds suffer from the significant disadvantage that they are (1) relatively impotent, which is important because the mass of drug that can be inhaled by the lung is limited; (2) rapidly absorbed, which limits the half-life of the drug on the mucosal surface; and (3) are freely dissociable from ENaC. The sum of these disadvantages embodied in these well known diuretics produces compounds with insufficient potency and/or effective half-life on mucosal surfaces to have therapeutic benefit for hydrating mucosal surfaces.

Clearly, what is needed are drugs that are more effective at restoring the clearance of mucus from the lungs of patients with CB/CF. The value of these new therapies will be reflected in improvements in the quality and duration of life for both the CF and the CB populations.

Other mucosal surfaces in and on the body exhibit subtle differences in the normal physiology of the protective surface liquids on their surfaces but the pathophysiology of disease reflects a common theme, i.e., too little protective surface liquid. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity. Similarly, keratoconjunctivitis sira (dry eye) is caused by failure of lacrimal glands to secrete liquid in the face of continued $Na^+$ dependent liquid absorption on conjunctional surfaces. In rhinosinusitis, there is an imbalance, as in CB, between mucin secretion and relative ASL depletion. Finally, in the gastrointestinal tract, failure to secrete $Cl^-$ (and liquid) in the proximal small intestine, combined with increased $Na^+$ (and liquid) absorption in the terminal ileum leads to the distal intestinal obstruction syndrome (DIOS). In older patients excessive $Na^+$ (and volume) absorption in the descending colon produces constipation and diverticulitis.

Fifty million Americans and hundreds of millions of others around the world suffer from high blood pressure and the subsequent sequale leading to congestive heart failure and increasing mortality. It is the Western World's leading killer and there is a need there for new medicines to treat these diseases. Thus, in addition, some of the novel sodium channel blockers of this invention can be designed to target the kidney and as such they may be used as diuretics for the treatment of hypertension, congestive heart failure (CHF) and other cardiovascular diseases. These new agents may be used alone or in combination with beta-blockers, ACE inhibitors, HMG-CoA reductase inhibitors, calcium channel blockers and other cardiovascular agents.

SUMMARY OF THE INVENTION

It is an object of the present invention to provide compounds that are more potent and/or absorbed less rapidly from mucosal surfaces, and/or are less reversible as compared to known compounds.

It is another aspect of the present invention to provide compounds that are more potent and/or absorbed less rapidly and/or exhibit less reversibility, as compared to compounds such as amilorde, benzamil, and phenamil. Therefore, the compounds will give a prolonged pharmacodynamic half-life on mucosal surfaces as compared to known compounds.

It is another object of the present invention to provide compounds which are (1) absorbed less rapidly from mucosal surfaces, especially airway surfaces, as compared to known compounds and; (2) when absorbed from musosal surfaces after administration to the mucosal surfaces, are converted in vivo into metabolic derivatives thereof which have reduced efficacy in blocking sodium channels as compared to the administered parent compound.

It is another object of the present invention to provide compounds that are more potent and/or absorbed less rapidly and/or exhibit less reversibility, as compared to compounds such as amiloride, benzamil, and phenamil. Therefore, such compounds will give a prolonged pharmacodynamic half-life on mucosal surfaces as compared to previous compounds.

It is another object of the present invention to provide compounds that target the kidney for use in the treatment of cardiovascular disease.

It is another object of the present invention to provide methods of treatment that take advantage of the pharmacological properties of the compounds described above.

In particular, it is an object of the present invention to provide methods of treatment which rely on rehydration of mucosal surfaces.

In particular, it is an object of the present invention to provide methods of treating cardiovascular disease.

The objects of the present invention may be accomplished with a class of pyrazinoylguanidine compounds represented by formula (I):

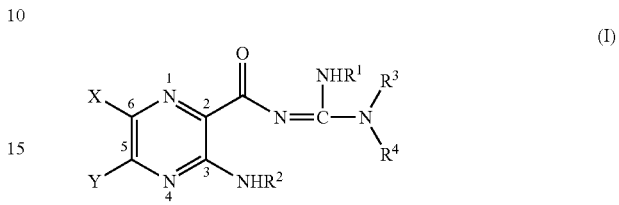

(I)

where

X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or $-N(R^2)_2$;

$R^1$ is hydrogen or lower alkyl;

each $R^2$ is, independently, $-R^7$, $-(CH_2)_m-OR^8$, $-(CH_2)$, $-NR^7R^{10}$, $-(CH_2)_n(CHOR^8)(CHOR^8)_n-CH_2OR^8$, $-(CH_2CH_2O)_n-R^8$, $-(CH_2CH_2O)_m-CH_2CH_2NR^7R^{10}$, $-(CH_2)_n-C(=O)NR^7R^{10}$, $-(CH_2)_n-Z_g-R^7$, $-(CH_2)_m-NR^{10}-CH_2(CHOR^8)(CHOR^8)_n-CH_2OR^8$, $-(CH_2)_n-CO_2R^7$, or

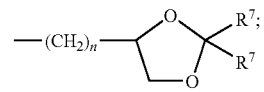

where when two $-CH_2OR^8$ groups are located 1,2- or 1,3- with respect to each other the $R^8$ groups may be joined to form a cyclic mono- or di-substituted 1,3-dioxane or 1,3-dioxolane;

$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

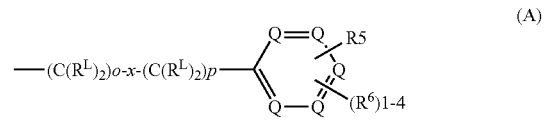

(A)

where each $R^L$ is, independently, $-R^7$, $-(CH_2)-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, —$(CH_2)_n$—$C(=O)NR^7R^{10}$, —$O$—$(CH_2)_m$—$C(=O)NR^7R^{10}$, —$(CH_2)_n$—$(Z)_g$—$R^7$, —$O$—$(CH_2)_m$—$(Z)_g$—$R^7$, —$(CH_2)_m$—$NR^{10}$—$CH_2(CHOR^8)(CHOR^8)_n$—$CH_2OR^8$, —$O$—$(CH_2)_m$—$NR^{10}$—$CH_2(CHOR^8)(CHOR^8)_n$—$CH_2OR^8$, —$(CH_2)_n$—$CO_2R^7$, —$O$—$(CH_2)_m$—$CO_2R^7$, —$OSO_3H$, —O-glucuronide, —O-glucose,

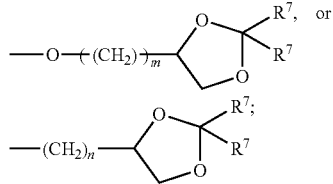

where when two —$CH_2OR^8$ groups are located 1,2- or 1,3- with respect to each other the $R^8$ groups may be joined to form a cyclic mono- or di-substituted 1,3-dioxane or 1,3-dioxolane;

each o is, independently, an integer from 0 to 10;

each p is an integer from 0 to 10;

with the proviso that the sum of o and p in each contiguous chain is from 1 to 10;

each x is, independently, O, $NR^{10}$, $C(=O)$, CHOH, $C(=N-R^{10})$, $CHNR^7R^{10}$, or represents a single bond;

each $R^5$ is, independently, —$(CH_2)_n$—$NR^{12}R^{12}$, —$O$—$(CH_2)_m$—$NR^{12}R^{12}$, —$O$—$(CH_2)_n$—$NR^{12}R^{12}$, —$O$—$(CH_2)_m$—$(Z)_gR^{12}$, —$(CH_2)_n NR^{11}R^{11}$, —$O$—$(CH_2)_m NR^{11}R^{11}$, —$(CH_2)_n$—$N^{\oplus}$—$(R^{11})_3$, —$O$—$(CH_2)_m$—$N^{\oplus}$—$(R^{11})_3$, —$(CH_2)_n$—$(Z)_g$—$(CH_2)_m$—$NR^{10}R^{10}$, —$O$—$(CH_2)_m$—$(Z)_g$—$(CH_2)_m$—$NR^{10}R^{10}$, —$(CH_2CH_2O)_m$—$CH_2CH_2NR^{12}R^{12}$, —$O$—$(CH_2CH_2O)_m$—$CH_2CH_2NR^{12}R^{12}$, —$(CH_2)_n$—$(C=O)NR^{12}R^{12}$, —$O$—$(CH_2)_m$—$(C=O)NR^{12}R^{12}$, —$O$—$(CH_2)_m$—$(CHOR^8)_m CH_2NR^{10}$—$(Z)_g$—$R^{10}$, —$(CH_2)_n$—$(CHOR^8)_m CH_2$—$NR^{10}$—$(Z)_g$—$R^{10}$, —$(CH_2)_n$—$NR^{10}$—$O(CH_2)_m(CHOR^8)_n CH_2NR^{10}$—$(Z)_g$—$R^{10}$, —$O(CH_2)_m$—$NR^{10}$—$(CH_2)_m$—$(CHOR^8)_n CH_2NR^{10}$—$(Z)_g$—$R^{10}$, —(Het)-$(CH_2)_m$—$OR^8$, -(Het)-$(CH_2)_m$—$NR^7R^{10}$, -(Het)-$(CH_2)_m(CHOR^8)(CHOR^8)_n$—$CH_2OR^8$, -(Het)-$(CH_2CH_2O)_m$—$R^8$, -(Het)-$(CH_2CH_2O)_m$—$CH_2CH_2NR^7R^{10}$, -(Het)-$(CH_2)_m$—$C(=O)NR^7R^{10}$, -(Het)-$(CH_2)_m$—$(Z)_g$—$R^7$, -(Het)-$(CH_2)_m$—$NR^{10}$—$CH_2(CHOR^8)(CHOR^8)_n$—$CH_2OR^8$, -(Het)-$(CH_2)_m$—$CO_2R^7$, -(Het)-$(CH_2)_m$—$NR^{12}R^{12}$, -(Het)-$(CH_2)_n$—$NR^{12}R^{12}$, -(Het)-$(CH_2)_m$—$(Z)_gR^{12}$, -(Het)-$(CH_2)_n NR^{11}R^{11}$, -(Het)-$(CH_2)_m$—$N^{\oplus}$—$(R^{11})_3$, -(Het)-$(CH_2)_m$—$(Z)_g$—$(CH_2)_m$—$NR^{10}R^{10}$, -(Het)-$(CH_2CH_2O)_m$—$CH_2CH_2NR^{12}R^{12}$, -(Het)-$(CH_2)_m$—$(C=O)NR^{12}R^{12}$, -(Het)-$(CH_2)_m$—$(CHOR^8)_m CH_2NR^{10}$—$(Z)_g$—$R^{10}$, -(Het)-$(CH_2)_m$—$NR^{10}$—$(CH_2)_m$—$(CHOR^8)_n CH_2NR^{10}$—$(Z)_g$—$R^{10}$, where when two —$CH_2OR^8$ groups are located 1,2- or 1,3- with respect to each other the $R^8$ groups may be joined to form a cyclic mono- or di-substituted 1,3-dioxane or 1,3-dioxolane, —$(CH_2)_n(CHOR^8)(CHOR^8)_n$—$CH_2OR^8$, with the proviso that two —$CH_2OR^8$ groups are located 1,2- or 1,3- with respect to each other and the $R^8$ groups are joined to form a cyclic mono or disubstituted 1,3-dioxane or 1,3-dioxolane, —$O$—$(CH_2)_m(CHOR^8)(CHOR^8)_n$—$CH_2OR^8$, with the proviso that two —$CH_2OR^8$ groups are located 1,2- or 1,3- with respect to each other and the $R^8$ groups are joined to form a cyclic mono or disubstituted 1,3-dioxane or 1,3-dioxolane, $(CH_2)_n$—$NR^{10}$—$CH_2(CHOR^8)(CHOR^8)_n$—$CH_2OR^8$, with the proviso that two —$CH_2OR^8$ groups are located 1,2- or 1,3- with respect to each other and the $R^8$ groups are joined to form a cyclic mono or disubstituted 1,3-dioxane or 1,3-dioxolane, or —$O$—$(CH_2)_m$—$NR^{10}$—$CH_2(CHOR^8)(CHOR^8)_n$—$CH_2OR^8$, with the proviso that two —$CH_2OR^8$ groups are located 1,2- or 1,3- with respect to each other and the $R^8$ groups are joined to form a cyclic mono or disubstituted 1,3-dioxane or 1,3-dioxolane;

each $R^6$ is, independently, —$R^5$, —$R^7$, —$OR^8$, —$N(R^7)_2$, —$(CH_2)_m$—$OR^8$, —$O$—$(CH_2)_m$—$OR^8$, —$(CH_2)_n$—$NR^7R^{10}$, —$O$—$(CH_2)$—$NR^7R^{10}$, —$(CH_2)_n(CHOR^8)(CHOR^8)_n$—$CH_2OR^8$, —$O$—$(CH_2)_m(CHOR^8)(CHOR^8)_n$—$CH_2OR^8$, —$(CH_2CH_2O)_m$—$R^8$, —$O$—$(CH_2CH_2O)_m$—$R^8$, —$(CH_2CH_2O)_m$—$CH_2CH_2NR^7R^{10}$, —$O$—$(CH_2CH_2O)_m$—$CH_2CH_2NR^7R^{10}$, —$(CH_2)_n$—$C(=O)NR^7R^{10}$, —$O$—$(CH_2)_m$—$C(=O)NR^7R^{10}$, —$(CH_2)_n$—$(Z)_g$—$R^7$, —$O$—$(CH_2)_m$—$(Z)_g$—$R^7$, —$(CH_2)_n$—$NR^{10}$—$CH_2(CHOR^8)(CHOR^8)_n$—$CH_2OR^8$, —$O$—$(CH_2)_m$—$NR^{10}$—$CH_2(CHOR^8)(CHOR^8)_n$—$CH_2OR^8$, —$(CH_2)_n$—$CO_2R^7$, —$O$—$(CH_2)_m$—$CO_2R^7$—$OSO_3H$, —O-glucuronide, —O-glucose,

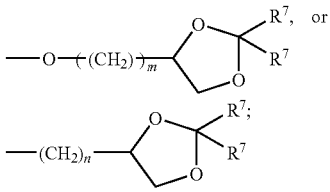

where when two $R^6$ are —$OR^{11}$ and are located adjacent to each other on a phenyl ring, the alkyl moieties of the two $R^6$ may be bonded together to form a methylenedioxy group and where when two —$CH_2OR^8$ groups are located 1,2- or 1,3- with respect to each other the $R^8$ groups may be joined to form a cyclic mono- or di-substituted 1,3-dioxane or 1,3-dioxolane;

each $R^7$ is, independently, hydrogen or lower alkyl;

each $R^8$ is, independently, hydrogen, lower alkyl, —$C(=O)$—$R^{11}$, glucuronide, 2-tetrahydropyranyl, or

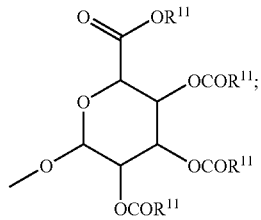

each $R^9$ is, independently, —$CO_2R^7$, —$CON(R^7)_2$, —$SO_2CH_3$, or —$C(=O)R^7$;

each $R^{10}$ is, independently, —H, —$SO_2CH_3$, —$CO_2R^7$, —$C(=O)NR^7R^9$, —$C(=O)R^7$, or —$CH_2$—$(CHOH)_n$—$CH_2OH$;

each Z is, independently, CHOH, $C(=O)$, $CHNR^7R^{10}$, $C=NR^{10}$, or $NR^{10}$;

each $R^{11}$ is, independently, lower alkyl;

each $R^{12}$ is independently, —$SO_2CH_3$, —$CO_2R^7$, —$C(=O)NR^7R^9$, —$C(=O)R^7$, or —$CH_2$—$(CHOH)_n$—$CH_2OH$;

each Het is independently, —$NR^7$, —$NR^{10}$, —S—, —SO—, or —$SO_2$—;

each g is, independently, an integer from 1 to 6;
each m is, independently, an integer from 1 to 7;
each n is, independently, an integer from 0 to 7;
each Q is, independently, C—$R^5$, C—$R^6$, or a nitrogen atom, wherein at
most three Q in a ring are nitrogen atoms;
or a pharmaceutically acceptable salt thereof, and
inclusive of all enantiomers, diastereomers, and racemic mixtures thereof.

The present also provides pharmaceutical compositions which contain a compound described above.

The present invention also provides a method of promoting hydration of mucosal surfaces, comprising:
administering an effective amount of a compound represented by formula (I) to a mucosal surface of a subject.

The present invention also provides a method of restoring mucosal defense, comprising:
topically administering an effective amount of compound represented by formula (I) to a mucosal surface of a subject in need thereof.

The present invention also provides a method of blocking ENaC, comprising:
contacting sodium channels with an effective amount of a compound represented by formula (I).

The present invention also provides a method of promoting mucus clearance in mucosal surfaces, comprising:
administering an effective amount of a compound represented by formula (I) to a mucosal surface of a subject.

The present invention also provides a method of treating chronic bronchitis, comprising:
administering an effective amount of a compound represented by formula (I) to a subject in need thereof.

The present invention also provides a method of treating cystic fibrosis, comprising:
administering an effective amount of compound represented by formula (I) to a subject in need thereof.

The present invention also provides a method of treating rhinosinusitis, comprising:
administering an effective amount of a compound represented by a formula (I) to a subject in need thereof.

The present invention also provides a method of treating nasal dehydration, comprising:
administering an effective amount of a compound represented by formula (I) to the nasal passages of a subject in need thereof.

In a more specific embodiment, the nasal dehydration is brought on by administering dry oxygen to the subject.

The present invention also provides a method of treating sinusitis, comprising:
administering an effective amount of a compound represented by formula (I) to a subject in need thereof.

The present invention also provides a method of treating pneumonia, comprising:
administering an effective amount of a compound represented by formula (I) to a subject in need thereof.

The present invention also provides a method of preventing ventilator-induced pneumonia, comprising:
administering an effective compound represented by formula (I) to a subject by means of a ventilator.

The present invention also provides a method of treating asthma, comprising:
administering an effective amount of a compound represented by formula (I) to a subject in need thereof.

The present invention also provides a method of treating primary ciliary dyskinesia, comprising:
administering an effective amount of a compound represented by formula (I) to a subject in need thereof.

The present invention also provides a method of treating otitis media, comprising:
administering an effective amount of a compound represented by formula (I) to a subject in need thereof.

The present invention also provides a method of inducing sputum for diagnostic purposes, comprising:
administering an effective amount of compound represented by formula (I) to a subject in need thereof.

The present invention also provides a method of treating chronic obstructive pulmonary disease, comprising:
administering an effective amount of a compound represented by formula (I) to a subject in need thereof.

The present invention also provides a method of treating emphysema, comprising:
administering an effective amount of a compound represented by formula (I) to a subject in need thereof.

The present invention also provides a method of treating dry eye, comprising:
administering an effective amount of a compound represented by formula (I) to the eye of the subject in need thereof.

The present invention also provides a method of promoting ocular hydration, comprising:
administering an effective amount of a compound represented by formula (I) to the eye of the subject.

The present invention also provides a method of promoting corneal hydration, comprising:
administering an effective amount of a compound represented by formula (I) to the eye of the subject.

The present invention also provides a method of treating Sjögren's disease, comprising:
administering an effective amount of compound represented by formula (I) to a subject in need thereof.

The present invention also provides a method of treating vaginal dryness, comprising:
administering an effective amount of a compound represented by formula (I) to the vaginal tract of a subject in need thereof.

The present invention also provides a method of treating dry skin, comprising:
administering an effective amount of a compound represented by formula (I) to the skin of a subject in need thereof.

The present invention also provides a method of treating dry mouth (xerostomia), comprising:
administering an effective amount of compound represented by formula (I) to the mouth of the subject in need thereof.

The present invention also provides a method of treating distal intestinal obstruction syndrome, comprising:
administering an effective amount of a compound represented by formula (I) to a subject in need thereof.

The present invention also provides a method of treating esophagitis, comprising:
administering an effective amount of a compound represented by formula (I) to a subject in need thereof.

The present invention also provides a method of treating constipation, comprising:
administering an effective amount of a compound represented by formula (I) to a subject in need thereof. In one embodiment of this method, the compound is administered either orally or via a suppository or enema.

The present invention also provides a method of treating chronic diverticulitis comprising:
administering an effective amount of a compound represented by formula (I) to a subject in need thereof.

The present invention also provides a method of treating hypertension, comprising administering the compound represented by formula (I) to a subject in need thereof.

The present invention also provides a method of reducing blood pressure, comprising administering the compound represented by formula (I) to a subject in need thereof.

The present invention also provides a method of treating edema, comprising administering the compound represented by formula (I) to a subject in need thereof.

The present invention also provides a method of promoting diuresis, comprising administering the compound represented by formula (I) to a subject in need thereof.

The present invention also provides a method of promoting natriuresis, comprising administering the compound represented by formula (I) to a subject in need thereof.

The present invention also provides a method of promoting saluresis, comprising administering the compound represented by formula (I) to a subject in need thereof.

A more complete appreciation of the invention and many of the attendant advantages thereof will be readily obtained as the same becomes better understood by reference to the following detailed description.

DETAILED DESCRIPTION OF THE INVENTION

The present invention is based on the discovery that the compounds of formula (I) are more potent and/or, absorbed less rapidly from mucosal surfaces, especially airway surfaces, and/or less reversible from interactions with ENaC as compared to compounds such as amiloride, benzamil, and phenamil. Therefore, the compounds of formula (I) have a longer half-life on mucosal surfaces as compared to these compounds.

The present invention is also based on the discovery that certain compounds embraced by formula (I) are converted in vivo into metabolic derivatives thereof that have reduced efficacy in blocking sodium channels as compared to the parent administered compound, after they are absorbed from mucosal surfaces after administration. This important property means that the compounds will have a lower tendency to cause undesired side-effects by blocking sodium channels located at untargeted locations in the body of the recipient, e.g., in the kidneys.

The present invention is also based on the discovery that certain compounds embraced by formula (I) target the kidney and thus may be used as cardiovascular agents.

In the compounds represented by formula (I), X may be hydrogen, halogen, trifluoromethyl, lower alkyl, lower cycloalkyl, unsubstituted or substituted phenyl, lower alkyl-thio, phenyl-lower alkyl-thio, lower alkyl-sulfonyl, or phenyl-lower alkyl-sulfonyl. Halogen is preferred.

Examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges there between, such as 1, 2, 3, 4, 5, 6, and 7 carbon atoms. The term "alkyl" embraces all types of such groups, e.g., linear, branched, and cyclic alkyl groups. This description is applicable to the term "lower alkyl" as used throughout the present disclosure. Examples of suitable lower alkyl groups include methyl, ethyl, propyl, cyclopropyl, butyl, isobutyl, etc.

Substituents for the phenyl group include halogens. Particularly preferred halogen substituents are chlorine and bromine.

Y may be hydrogen, hydroxyl, mercapto, lower alkoxy, lower alkyl-thio, halogen, lower alkyl, lower cycloalkyl, mononuclear aryl, or $—N(R^2)_2$. The alkyl moiety of the lower alkoxy groups is the same as described above. Examples of mononuclear aryl include phenyl groups. The phenyl group may be unsubstituted or substituted as described above. The preferred identity of Y is $—N(R^2)_2$. Particularly preferred are such compounds where each $R^2$ is hydrogen.

$R^1$ may be hydrogen or lower alkyl. Hydrogen is preferred for $R^1$.

Each $R^2$ may be, independently, $—R^7$, $—(CH_2)_m—OR^8$, $—(CH_2)_m—NR^7R^{10}$, $—(CH_2)_n(CHOR^8)(CHOR^8)_n—CH_2OR^8$, $—(CH_2CH_2O)_m—R^8$, $—(CH_2CH_2O)_m—CH_2CH_2NR^7R^{10}$, $—(CH_2)_n—C(=O)NR^7R^{10}$, $—(CH_2)_n—Z_g—R^7$, $—(CH_2)_m—NR^{10}—CH_2(CHOR^8)(CHOR^8)_n—CH_2OR^8$, $—(CH_2)_n—CO_2R^7$, or

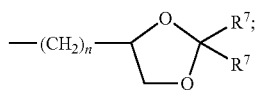

In the definition of $R^2$ described above, when two $—CH_2OR^8$ groups are located 1,2- or 1,3- with respect to each other the $R^8$ groups may be joined to form a cyclic mono- or di-substituted 1,3-dioxane or 1,3-dioxolane.

Hydrogen and lower alkyl, particularly $C_1$-$C_3$ alkyl are preferred for $R^2$. Hydrogen is particularly preferred.

$R^3$ and $R^4$ may be, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, provided that at least one of $R^3$ and $R^4$ is a group represented by formula (A).

Preferred compounds are those where one of $R^3$ and $R^4$ is hydrogen and the other is represented by formula (A).

In formula (A), the moiety $—(C(R^L)_2)_o$-x-$(C(R^L)_2)_p—$ defines an alkylene group bonded to the aromatic ring. The variables o and p may each be an integer from 0 to 10, subject to the proviso that the sum of o and p in the chain is from 1 to 10. Thus, o and p may each be 0, 1, 2, 3, 4, 5, 6, 7, 8, 9, or 10. Preferably, the sum of o and p is from 2 to 6. In a particularly preferred embodiment, the sum of o and p is 4.

The linking group in the alkylene chain, x, may be, independently, O, $NR^{10}$, $C(=O)$, CHOH, $C(=N—R^{10})$, $CHNR^7R^{10}$, or represents a single bond;

Therefore, when x represents a single bond, the alkylene chain bonded to the ring is represented by the formula $—(C(R^L)_2)_{o+p}—$, in which the sum o+p is from 1 to 10.

Each $R^L$ may be, independently, $—R^7$, $—(CH_2)_n—OR^8$, $—O—(CH_2)_m—R^8$, $—(CH_2)_m—NR^7R^{10}$, $—O—(CH_2)_m—NR^7R^{10}$, $—(CH_2)_n(CHOR^8)(CHOR^8)_n—CH_2OR^8$, $—O—(CH_2)_m(CHOR^8)(CHOR^8)_n—CH_2OR^8$, $—(CH_2CH_2O)_m—R^8$, $—O—(CH_2CH_2O)_m—R^8$, $—(CH_2CH_2O)_m—CH_2CH_2NR^7R^{10}$, $—O—(CH_2CH_2O)_m—CH_2CH_2NR^7R^{10}$, $—(CH_2)_m—C(=O)NR^7R^{10}$, $—O—(CH_2)_m—C(=O)NR^7R^{10}$, $—(CH_2)_n—(Z)_g—R^7$, $—O—(CH_2)_m—(Z)_g—R^7$, $—(CH_2)_n—NR^{10}—CH_2(CHOR^8)(CHOR^8)_n—CH_2OR^8$, $—O—(CH_2)_m—NR^{10}—CH_2(CHOR^8)(CHOR^8)_n—CH_2OR^8$, $—(CH_2)_n—CO_2R^7$, $—O—(CH_2)_m—CO_2R^7$, $—OSO_3H$, $—O$-glucuronide, $—O$-glucose,

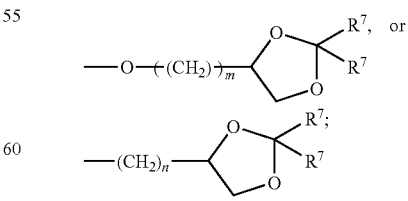

In the definition of $R^L$ above, when two $—CH_2OR^8$ groups are located 1,2- or 1,3- with respect to each other the $R^8$ groups may be joined to form a cyclic mono- or di-substituted 1,3-dioxane or 1,3-dioxolane.

The preferred $R^L$ groups include —H, —OH, —N($R^7$)$_2$, especially where each $R^7$ is hydrogen.

In the alkylene chain in formula (A), it is preferred that when one $R^L$ group bonded to a carbon atoms is other than hydrogen, then the other $R^L$ bonded to that carbon atom is hydrogen, i.e., the formula —CHR$^L$—. It is also preferred that at most two $R^L$ groups in an alkylene chain are other than hydrogen, where in the other $R^L$ groups in the chain are hydrogens. Even more preferably, only one $R^L$ group in an alkylene chain is other than hydrogen, where in the other $R^L$ groups in the chain are hydrogens. In these embodiments, it is preferable that x represents a single bond.

In another particular embodiment of the invention, all of the $R^L$ groups in the alkylene chain are hydrogen. In these embodiments, the alkylene chain is represented by the formula

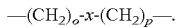

Each $R^5$ is independently, —(CH$_2$)$_n$—NR$^{12}$R$^{12}$, —O—(CH$_2$)$_m$—NR$^{12}$R$^{12}$, —O—(CH$_2$)$_n$—NR$^{12}$R$^{12}$, —O—(CH$_2$)$_m$—(Z)$_g$R$^{12}$, —(CH$_2$)$_n$NR$^{11}$R$^{11}$, —O—(CH$_2$)$_m$—NR$^{11}$R$^{11}$, —(CH$_2$)$_n$—N$^\oplus$—(R$^{11}$)$_3$, —O—(CH$_2$)$_m$—N$^\oplus$—(R$^{11}$)$_3$, —(CH$_2$)$_n$—(Z)$_g$—(CH$_2$)$_m$—NR$^{10}$R$^{10}$, —O—(CH$_2$)$_n$—(Z)$_g$—(CH$_2$)$_m$—NR$^{10}$R$^{10}$, —(CH$_2$CH$_2$)$_m$—CH$_2$CH$_2$NR$^{12}$R$^{12}$, —O—(CH$_2$CH$_2$O)$_m$—CH$_2$CH$_2$NR$^{12}$R$^{12}$, —(CH$_2$)$_n$—(C=O)NR$^{12}$R$^{12}$, —O—(CH$_2$)$_m$—(C=O)NR$^{12}$R$^{12}$, —O—(CH$_2$)$_m$—(CHOR$^8$)$_m$CH$_2$NR$^{10}$—(Z)$_g$—R$^{10}$, —(CH$_2$)$_n$—(CHOR$^8$)$_m$CH$_2$—NR$^{10}$—(Z)$_g$-R$^{10}$, —(CH$_2$)$_n$NR$^{10}$—O(CH$_2$)$_m$(CHOR$^8$)$_n$CH$_2$NR$^{10}$—(Z)$_g$—R$^{10}$, —O(CH$_2$)$_m$—NR$^{10}$—(CH$_2$)$_m$—(CHOR$^8$)$_n$CH$_2$NR$^{10}$—(Z)$_g$—R$^{10}$, -(Het)-(CH$_2$)$_m$—OR$^8$, -(Het)-(CH$_2$)$_m$—NR$^7$R$^{10}$, -(Het)-(CH$_2$)$_m$(CHOR$^8$)(CHOR$^8$)$_n$—CH$_2$OR$^8$, -(Het)-(CH$_2$CH$_2$O)$_m$—R$^8$, -(Het)-(CH$_2$CH$_2$O)$_m$—CH$_2$CH$_2$NR$^7$R$^{10}$, -(Het)-(CH$_2$)$_m$—C(=O)NR$^7$R$^{10}$, -(Het)-(CH$_2$)$_m$—(Z)$_g$—R$^7$, -(Het)-(CH$_2$)$_m$—NR$^{10}$—CH$_2$(CHOR$^8$)(CHOR$^8$)$_n$—CH$_2$OR$^8$, -(Het)-(CH$_2$)$_m$—CO$_2$R$^7$, -(Het)-(CH$_2$)$_m$—NR$^{12}$R$^{12}$, -(Het)-(CH$_2$)$_n$—NR$^{12}$R$^{12}$, -(Het)-(CH$_2$)$_m$—(Z)$_g$R$^{12}$, -(Het)-(CH$_2$)$_m$NR$^{11}$R$^{11}$, -(Het)-(CH$_2$)$_m$—N$^\oplus$—(R$^{11}$)$_3$, -(Het)-(CH$_2$)$_m$—(Z)$_g$—(CH$_2$)$_m$—NR$^{10}$R$^{10}$, -(Het)-(CH$_2$CH$_2$O)$_m$—CH$_2$CH$_2$NR$^{12}$R$^{12}$, -(Het)-(CH$_2$)$_m$—(C=O)NR$^{12}$R$^{12}$, -(Het)-(CH$_2$)$_m$—(CHOR$^8$)$_m$CH$_2$NR$^{10}$—(Z)$_g$—R$^{10}$, -(Het)-(CH$_2$)$_m$—NR$^{10}$—(CH$_2$)$_m$—(CHOR$^8$)$_n$CH$_2$NR$^{10}$—(Z)$_g$—R$^{10}$, where when two —CH$_2$OR$^8$ groups are located 1,2- or 1,3- with respect to each other the R$^8$ groups may be joined to form a cyclic mono- or di-substituted 1,3-dioxane or 1,3-dioxolane, —(CH$_2$)$_n$(CHOR$^8$)(CHOR$^8$)$_n$—CH$_2$OR$^8$, with the proviso that two —CH$_2$OR$^8$ groups are located 1,2- or 1,3- with respect to each other and the R$^8$ groups are joined to form a cyclic mono or disubstituted 1,3-dioxane or 1,3-dioxolane, —O—(CH$_2$)$_m$(CHOR$^8$)(CHOR$^8$)$_n$—CH$_2$OR$^8$, with the proviso that two —CH$_2$OR$^8$ groups are located 1,2- or 1,3- with respect to each other and the R$^8$ groups are joined to form a cyclic mono or disubstituted 1,3-dioxane or 1,3-dioxolane, —(CH$_2$)$_n$—NR$^{10}$—CH$_2$(CHOR$^8$)(CHOR$^8$)$_n$—CH$_2$OR$^8$, with the proviso that two —CH$_2$OR$^8$ groups are located 1,2- or 1,3- with respect to each other and the R$^8$ groups are joined to form a cyclic mono or disubstituted 1,3-dioxane or 1,3-dioxolane, or —O—(CH$_2$)$_m$—NR$^{10}$—CH$_2$(CHOR$^8$)(CHOR$^8$)$_n$—CH$_2$OR$^8$, with the proviso that two —CH$_2$OR$^8$ groups are located 1,2- or 1,3- with respect to each other and the R$^8$ groups are joined to form a cyclic mono or disubstituted 1,3-dioxane or 1,3-dioxolane.

Preferred examples of $R^5$ include:
—N(SO$_2$CH$_3$)$_2$,
—CH$_2$—CHNHBocCO$_2$CH$_3$ (α),
—O—CH$_2$—CHNH$_2$CO$_2$H (α),
—O—CH$_2$—CHNH$_2$CO$_2$CH$_3$ (α),
—O—(CH$_2$)$_2$—N$^+$(CH$_3$)$_3$,
—C(=O)N—H—(CH$_2$)$_2$—NH$_2$,
—C(=O)NH—(CH$_2$)$_2$—NH—C(=NH)—NH$_2$, and

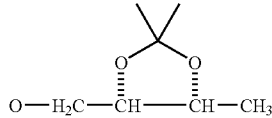

There are four $R^6$ groups present on the ring in formula (A). Each $R^6$ may be each, independently, $R^5$ as described above, —R$^7$, —OR$^8$, —N(R$^7$)$_2$, —(CH$_2$)$_m$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose, or

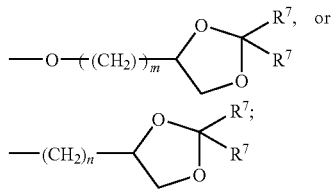

When two $R^6$ are —OR$^{11}$ and are located adjacent to each other on a phenyl ring, the alkyl moieties of the two $R^6$ groups may be bonded together to form a methylenedioxy group, i.e., a group of the formula —O—CH$_2$—O—. Also, when two —CH$_2$OR$^8$ groups are located 1,2- or 1,3- with respect to each other the R$^8$ groups may be joined to form a cyclic mono- or di-substituted 1,3-dioxane or 1,3-dioxolane.

As discussed above, $R^6$ may be hydrogen. Therefore, 1, 2, 3, or 4 $R^6$ groups may be other than hydrogen. Preferably at most 3 of the $R^6$ groups are other than hydrogen.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n maybe 0, 1, 2, 3, 4, 5, 6, or 7.

Each Q in formula (A) is C—R$^5$, C—R$^6$, or a nitrogen atom, where at most three Q in a ring are nitrogen atoms. Thus, there may be 1, 2, or 3 nitrogen atoms in a ring. Preferably, at most two Q are nitrogen atoms. More preferably, at most one Q is a nitrogen atom. In one particular embodiment, the nitrogen atom is at the 3-position of the ring. In another embodiment of the invention, each Q is either C—R$^5$ or C—R$^6$, i.e., there are no nitrogen atoms in the ring.

More specific examples of suitable groups represented by formula (A) are shown in formulas (B)-(F) below:

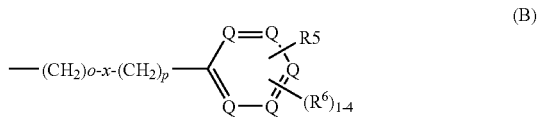

(B)

where o, x, p, $R^5$, and $R^6$, are as defined above;

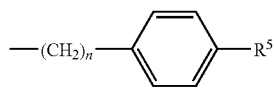

(C)

where n is an integer from 1 to 10 and $R^5$ is as defined above;

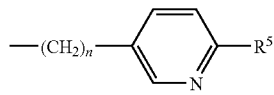

(D)

where n is an integer from 1 from 10 and $R^5$ is as defined above;

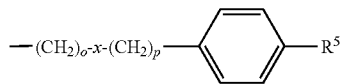

(E)

where o, x, p, and $R^5$ are as defined above;

In a preferred embodiment of the invention, Y is —$NH_2$.
In another preferred embodiment, $R^2$ is hydrogen.
In another preferred embodiment, $R^1$ is hydrogen.
In another preferred embodiment, X is chlorine.
In another preferred embodiment, $R^3$ is hydrogen.
In another preferred embodiment, $R^L$ is hydrogen.
In another preferred embodiment, o is 4.
In another preferred embodiment, p is 0.
In another preferred embodiment, the sum of o and p is 4.
In another preferred embodiment, x represents a single bond.
In another preferred embodiment, $R^6$ is hydrogen.
In another preferred embodiment, at most one Q is a nitrogen atom.
In another preferred embodiment, no Q is a nitrogen atom.
In a preferred embodiment of the present invention:
X is halogen;
Y is —$N(R^7)_2$;
$R^1$ is hydrogen or $C_1$-$C_3$ alkyl;
$R^2$ is —$R^7$, —$OR^7$, $CH_2OR^7$, or —$CO_2R^7$;
$R^3$ is a group represented by formula (A); and
$R^4$ is hydrogen, a group represented by formula (A), or lower alkyl;
In another preferred embodiment of the present invention:
X is chloro or bromo;
Y is —$N(R^7)_2$;
$R^2$ is hydrogen or $C_1$-$C_3$ alkyl;
at most three $R^6$ are other than hydrogen as described above;
at most three $R^L$ are other than hydrogen as described above; and
at most 2 Q are nitrogen atoms.
In another preferred embodiment of the present invention:
Y is —$NH_2$;
In another preferred embodiment of the present invention:
$R^4$ is hydrogen;
at most one $R^L$ is other than hydrogen as described above;
at most two $R^6$ are other than hydrogen as described above; and
at most 1 Q is a nitrogen atom.
Preferred examples of $R^5$ in the embodiments described above include:
—$N(SO_2CH_3)_2$,
—$CH_2$—$CHNHBocCO_2CH_3$ (α),
—O—$CH_2$—$CHNH_2CO_2H$ (α),
—O—$CH_2$—$CHNH_2CO_2CH_3$ (α),
—O—$(CH_2)_2$—$N^+(CH_3)_3$,
—C(=O)NH—$(CH_2)_2$—$NH_2$, and
—C(=O)NH—$(CH_2)_2$—NH—C(=NH)—$NH_2$.
Examples of compounds of the present invention include the following:

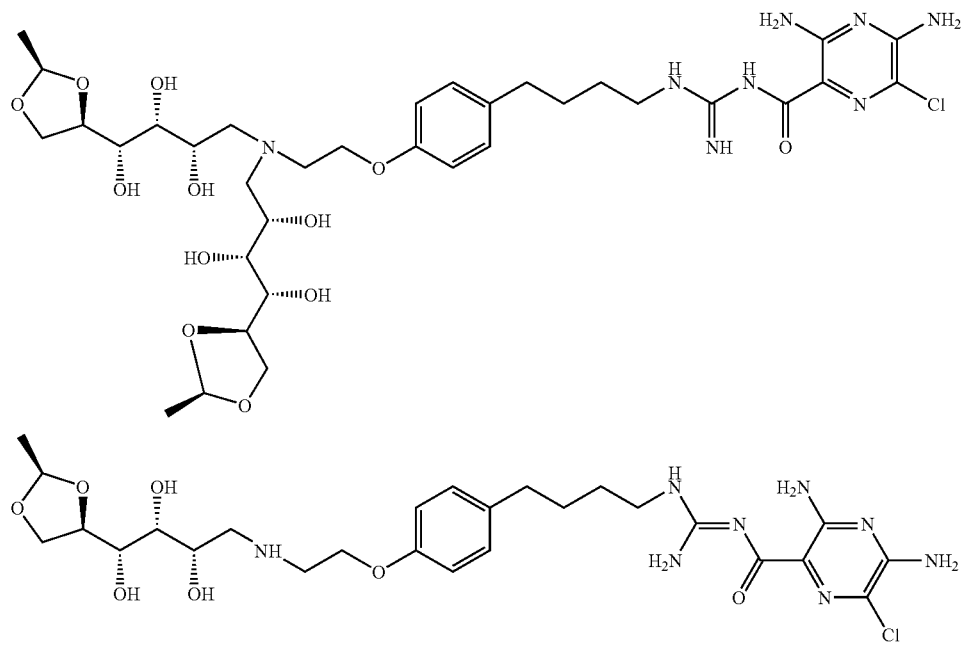

-continued

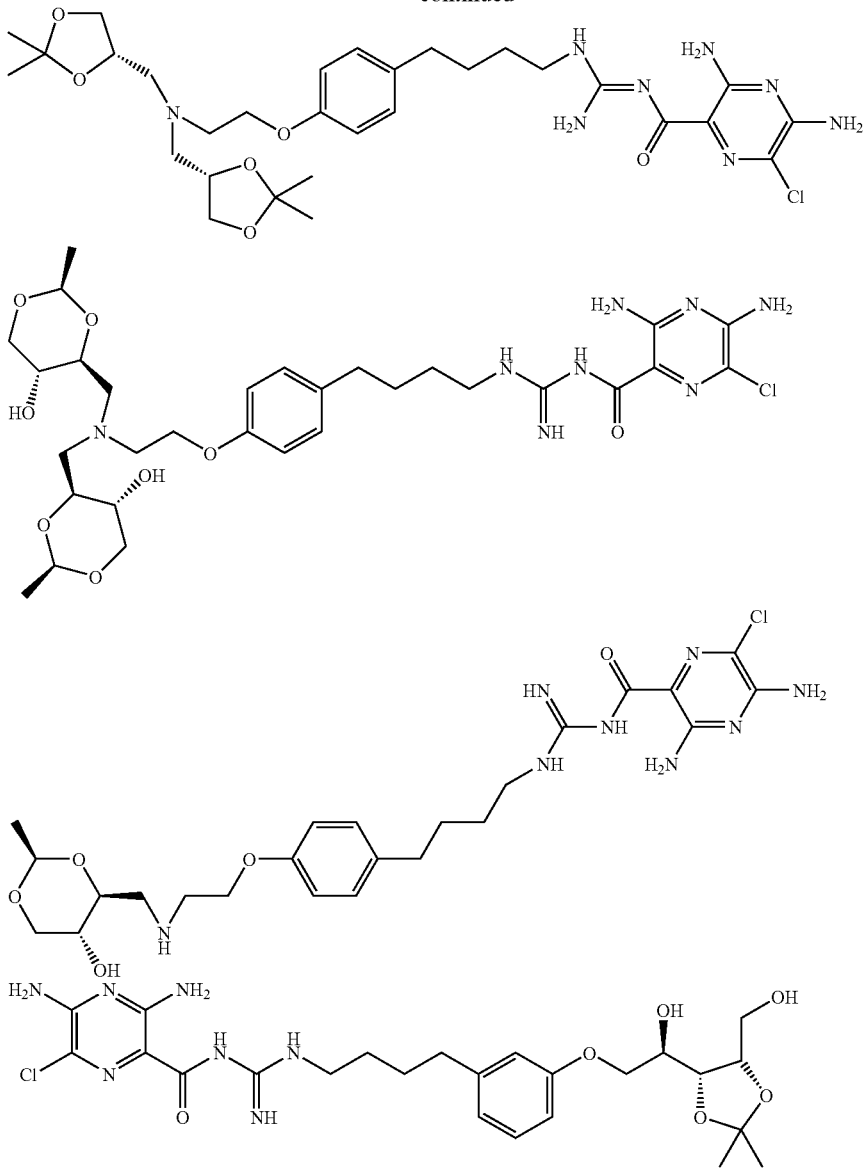

The compounds of formula (I) may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures of compounds within the scope of formula (I) are embraced by the present invention. All mixtures of such enantiomers and diastereomers are within the scope of the present invention.

Without being limited to any particular theory, it is believed that the compounds of formula (I) function in vivo as sodium channel blockers. By blocking epithelial sodium channels present in mucosal surfaces the compounds of formula (I) reduce the absorption of water by the mucosal surfaces. This effect increases the volume of protective liquids on mucosal surfaces, rebalances the system, and thus treats disease.

The present invention also provides methods of treatment that take advantage of the properties of the compounds of formula (I) discussed above. Thus, subjects that may be treated by the methods of the present invention include, but are not limited to, patients afflicted with cystic fibrosis, primary ciliary dyskinesia, chronic bronchitis, chronic obstructive airway disease, artificially ventilated patients, patients with acute pneumonia, etc. The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders) or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., *staphylococcus* infections such as *Staphylococcus aureus* infections, *Hemophilus influenza* infections, *Streptococcus pneumoniae* infections, *Pseudomonas aeuriginosa* infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, Rhinosinusitis. The invention may be administered to rhino-signal surfaces by topical delivery, including aerosols and drops.

The present invention may be used to hydrate mucosal surfaces other than airway surfaces. Such other mucosal surfaces include gastrointestinal surfaces, oral surfaces, genitourethral surfaces, ocular surfaces or surfaces of the eye, the inner ear and the middle ear. For example, the active compounds of the present invention may be administered by any suitable means, including locally/topically, orally, or rectally, in an effective amount.

The compounds of the present invention are also useful for treating a variety of functions relating to the cardiovascular system. Thus, the compounds of the present invention are useful for use as antihypertensive agents. The compounds may also be used to reduce blood pressure and to treat edema. In addition, the compounds of the present invention are also useful for promoting diuresis, natriuresis, and saluresis. The compounds may be used alone or in combination with beta blockers, ACE inhibitors, HMGCoA reductase inhibitors, calcium channel blockers and other cardiovascular agents to treat hypertension, congestive heart failure and reduce cardiovascular mortality.

The present invention is concerned primarily with the treatment of human subjects, but may also be employed for the treatment of other mammalian subjects, such as dogs and cats, for veterinary purposes.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution is not available to induce a physiological response, but serves as a depot of bioavailable drug which gradually dissolves into solution.

Another aspect of the present invention is a pharmaceutical composition, comprising a compound of formula (I) in a pharmaceutically acceptable carrier (e.g., an aqueous carrier solution). In general, the compound of formula (I) is included in the composition in an amount effective to inhibit the reabsorption of water by mucosal surfaces.

The compounds of the present invention may also be used in conjunction with a P2Y2 receptor agonist or a pharmaceutically acceptable salt thereof (also sometimes referred to as an "active agent" herein). The composition may further comprise a P2Y2 receptor agonist or a pharmaceutically acceptable salt thereof (also sometimes referred to as an "active agent" herein). The P2Y2 receptor agonist is typically included in an amount effective to stimulate chloride and water secretion by airway surfaces, particularly nasal airway surfaces. Suitable P2Y2 receptor agonists are described in columns 9-10 of U.S. Pat. No. 6,264,975, U.S. Pat. No. 5,656, 256, and U.S. Pat. No. 5,292,498, each of which is incorporated herein by reference.

Bronchodiloators can also be used in combination with compounds of the present invention. These bronchodilators include, but are not limited to, β-adrenergic agonists including but not limited to epinephrine, isoproterenol, fenoterol, albuterol, terbutalin, pirbuterol, bitolterol, metaproterenol, isoetharine, salmeterol xinafoate, as well as anticholinergic agents including but not limited to ipratropium bromide, as well as compounds such as theophylline and aminophylline. These compounds may be administered in accordance with known techniques, either prior to or concurrently with the active compounds described herein.

Another aspect of the present invention is a pharmaceutical formulation, comprising an active compound as described above in a pharmaceutically acceptable carrier (e.g., an aqueous carrier solution). In general, the active compound is included in the composition in an amount effective to treat mucosal surfaces, such as inhibiting the reabsorption of water by mucosal surfaces, including airway and other surfaces.

The active compounds disclosed herein may be administered to mucosal surfaces by any suitable means, including topically, orally, rectally, vaginally, ocularly and dermally, etc. For example, for the treatment of constipation, the active compounds may be administered orally or rectally to the gastrointestinal mucosal surface. The active compound may be combined with a pharmaceutically acceptable carrier in any suitable form, such as sterile physiological or dilute saline or topical solution, as a droplet, tablet or the like for oral administration, as a suppository for rectal or genitourethral administration, etc. Excipients may be included in the formulation to enhance the solubility of the active compounds, as desired.

The active compounds disclosed herein may be administered to the airway surfaces of a patient by any suitable means, including as a spray, mist, or droplets of the active compounds in a pharmaceutically acceptable carrier such as physiological or dilute saline solutions or distilled water. For example, the active compounds may be prepared as formulations and administered as described in U.S. Pat. No. 5,789,391 to Jacobus, the disclosure of which is incorporated by reference herein in its entirety.

Solid or liquid particulate active agents prepared for practicing the present invention could, as noted above, include particles of respirable or non-respirable size; that is, for respirable particles, particles of a size sufficiently small to pass through the mouth and larynx upon inhalation and into the bronchi and alveoli of the lungs, and for non-respirable particles, particles sufficiently large to be retained in the nasal airway passages rather than pass through the larynx and into the bronchi and alveoli of the lungs. In general, particles ranging from about 1 to 5 microns in size (more particularly, less than about 4.7 microns in size) are respirable. Particles of non-respirable size are greater than about 5 microns in size, up to the size of visible droplets. Thus, for nasal administration, a particle size in the range of 10-500 μm may be used to ensure retention in the nasal cavity.

In the manufacture of a formulation according to the invention, active agents or the physiologically acceptable salts or free bases thereof are typically admixed with, inter alia, an acceptable carrier. Of course, the carrier must be compatible with any other ingredients in the formulation and must not be deleterious to the patient. The carrier must be solid or liquid, or both, and is preferably formulated with the compound as a unit-dose formulation, for example, a capsule, that may contain 0.5% to 99% by weight of the active compound. One or more active compounds may be incorporated in the formulations of the invention, which formulations may be prepared by any of the well-known techniques of pharmacy consisting essentially of admixing the components.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate active agent composition may optionally contain a dispersant which serves to facilitate the formulation of an aerosol. A suitable dispersant is lactose, which may be blended with the active agent in any suitable ratio (e.g., a 1 to 1 ratio by weight).

Active compounds disclosed herein may be administered to airway surfaces including the nasal passages, sinuses and lungs of a subject by a suitable means know in the art, such as by nose drops, mists, etc. In one embodiment of the invention, the active compounds of the present invention and administered by transbronchoscopic lavage. In a preferred embodiment of the invention, the active compounds of the present invention are deposited on lung airway surfaces by administering an aerosol suspension of respirable particles comprised of the active compound, which the subject inhales. The respirable particles may be liquid or solid. Numerous inhalers for administering aerosol particles to the lungs of a subject are known.

Inhalers such as those developed by Inhale Therapeutic Systems, Palo Alto, Calif., USA, may be employed, including but not limited to those disclosed in U.S. Pat. Nos. 5,740,794; 5,654,007; 5,458,135; 5,775,320; and 5,785,049, all of which are incorporated herein by reference. The Applicant specifically intends that the disclosures of all patent references cited herein be incorporated by reference herein in their entirety. Inhalers such as those developed by Dura Pharmaceuticals, Inc., San Diego, Calif., USA, may also be employed, including but not limited to those disclosed in U.S. Pat. Nos. 5,622,166; 5,577,497; 5,645,051; and 5,492,112, all of which are incorporated herein by reference. Additionally, inhalers such as those developed by Aradigm Corp., Hayward, Calif., USA, may be employed, including but not limited to those disclosed in U.S. Pat. Nos. 5,826,570; 5,813,397; 5,819,726; and 5,655,516, all of which are incorporated herein by reference. These apparatuses are particularly suitable as dry particle inhalers.

Aerosols of liquid particles comprising the active compound may be produced by any suitable means, such as with a pressure-driven aerosol nebulizer or an ultrasonic nebulizer. See, e.g., U.S. Pat. No. 4,501,729, the contents of which is incorporated herein by reference. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. The carrier is typically water (and most preferably sterile, pyrogen-free water) or dilute aqueous alcoholic solution. Perfluorocarbon carriers may also be used. Optional additives include preservatives if the formulation is not made sterile, for example, methyl hydroxybenzoate, antioxidants, flavoring agents, volatile oils, buffering agents, and surfactants.

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing predetermined metered dose of medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of powder blend comprising the active ingredient, a suitable powder diluent, such as lactose, and an optional surfactant. The active ingredient typically comprises of 0.1 to 100% w/w of the formulation. A second type of illustrative aerosol generator comprises a metered dose inhaler. Metered dose inhalers are pressurized aerosol dispensers, typically containing a suspension or solution formulation of active ingredient in a liquified propellant. During use, these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one of more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferable from 30 to 150 liters per minute, and most preferably about 60 liters per minute. Aerosols containing greater amounts of medicament may be administered more rapidly.

The dosage of the active compounds disclosed herein will vary depending on the condition being treated and the state of the subject, but generally may be from about 0.01, 0.03, 0.05, 0.1 to 1, 5, 10 or 20 mg of the pharmaceutic agent, deposited on the airway surfaces. The daily dose may be divided among one or multiple unit dose administrations. The goal is to achieve a concentration of the pharmaceutic agents on lung airway surfaces of between $10^{-9}$-$10^4$ M.

In another embodiment, they are administered by administering an aerosol suspension of respirable or non-respirable particles (preferably non-respirable particles) comprised of active compound, which the subject inhales through the nose. The respirable or non-respirable particles may be liquid or solid. The quantity of active agent included may be an amount of sufficient to achieve dissolved concentrations of active agent on the airway surfaces of the subject of from about $10^{-9}$, $10^{-8}$, or $10^{-7}$ to about $10^{-3}$, $10^{-2}$, $10^{-1}$ moles/liter, and more preferably from about $10^{-9}$ to about $10^{-4}$ moles/liter.

The dosage of active compound will vary depending on the condition being treated and the state of the subject, but generally may be an amount sufficient to achieve dissolved concentrations of active compound on the nasal airway surfaces of the subject from about $10^{-9}$, $10^{-8}$, or $10^{-7}$ to about $10^{-3}$, $10^{-2}$, or $10^{-1}$ Moles/liter, and more preferably from about $10^{-7}$ to about $10^{-4}$ Moles/liter. Depending upon the solubility of the particular formulation of active compound administered, the daily dose may be divided among one or several unit dose administrations. The daily dose by weight may range from about 0.01, 0.03, 0.1, 0.5 or 1.0 to 10 or 20 milligrams of active agent particles for a human subject, depending upon the age and condition of the subject. A currently preferred unit dose is about 0.5 milligrams of active agent given at a regimen of 2-10 administrations per day. The dosage may be provided as a prepackaged unit by any suitable means (e.g., encapsulating a gelatin capsule).

In one embodiment of the invention, the particulate active agent composition may contain both a free base of active agent and a pharmaceutically acceptable salt to provide both early release and sustained release of active agent for dissolution into the mucus secretions of the nose. Such a composition serves to provide both early relief to the patient, and sustained relief over time. Sustained relief, by decreasing the number of daily administrations required, is expected to increase patient compliance with the course of active agent treatments.

Pharmaceutical formulations suitable for airway administration include formulations of solutions, emulsions, suspensions and extracts. See generally, J. Nairn, Solutions, Emulsions, Suspensions and Extracts, in Remington: The Science and Practice of Pharmacy, chap. 86 (19$^{th}$ ed 1995), incorporated herein by reference. Pharmaceutical formulations suitable for nasal administration may be prepared as described in U.S. Pat. Nos. 4,389,393 to Schor; 5,707,644 to Illum; 4,294,829 to Suzuki; and 4,835,142 to Suzuki, the disclosures of which are incorporated by reference herein.

Mists or aerosols of liquid particles comprising the active compound may be produced by any suitable means, such as by a simple nasal spray with the active agent in an aqueous pharmaceutically acceptable carrier, such as a sterile saline solution or sterile water. Administration may be with a pressure-driven aerosol nebulizer or an ultrasonic nebulizer. See e.g. U.S. Pat. Nos. 4,501,729 and 5,656,256, each of which is incorporated herein by reference. Suitable formulations for use in a nasal droplet or spray bottle or in nebulizers consist of the active ingredient in a liquid carrier, the active ingredient comprising up to 40% w/w of the formulation, but preferably less than 20% w/w. Typically the carrier is water (and most preferably sterile, pyrogen-free water) or dilute aqueous alcoholic solution, preferably made in a 0.12% to 0.8% solution of sodium chloride. Optional additives include preservatives if the formulation is not made sterile, for example, methyl hydroxybenzoate, antioxidants, flavoring agents, volatile oils, buffering agents, osmotically active agents (e.g. mannitol, xylitol, erythritol) and surfactants.

Compositions containing respirable or non-respirable dry particles of micronized active agent may be prepared by grinding the dry active agent with a mortar and pestle, and then passing the micronized composition through a 400 mesh screen to break up or separate out large agglomerates.

The particulate composition may optionally contain a dispersant which serves to facilitate the formation of an aerosol. A suitable dispersant is lactose, which may be blended with the active agent in any suitable ratio (e.g., a 1 to 1 ratio by weight).

The compounds of formula (I) may be synthesized according to procedures known in the art. A representative synthetic procedure is shown in the scheme below.

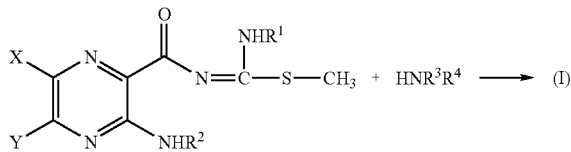

These procedures are described in, for example, E. J. Cragoe, "The Synthesis of Amiloride and Its Analogs" (Chapter 3) in *Amiloride and Its Analogs*, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813.

Several assays may be used to characterize the compounds of the present invention. Representative assays are discussed below.

In Vitro Measure of Sodium Channel Blocking Activity and Reversibility

One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Using chambers. Cells obtained from freshly excised human, dog, sheep or rodent airways are seeded onto porous 0.4 micron Snapwell™ Inserts (CoStar), cultured at air-liquid interface (ALI) conditions in hormonally defined media, and assayed for sodium transport activity ($I_{SC}$) while bathed in Krebs Bicarbonate Ringer (KBR) in Using chambers. All test drug additions are to the lumenal bath with half-log dose addition protocols (from $1\times10^{-11}$ M to $3\times10^{-5}$ M), and the cumulative change in $I_{SC}$ (inhibition) recorded. All drugs are prepared in dimethyl sulfoxide as stock solutions at a concentration of $1\times10^{-2}$ M and stored at $-20°$ C. Eight preparations are typically run in parallel; two preparations per run incorporate amiloride and/or benzamil as positive controls. After the maximal concentration ($5\times10^{-5}$ M) is administered, the lumenal bath is exchanged three times with fresh drug-free KBR solution, and the resultant $I_{SC}$ measured after each wash for approximately 5 minutes in duration. Reversibility is defined as the percent return to the baseline value for sodium current after the third wash. All data from the voltage clamps are collected via a computer interface and analyzed off-line.

Dose-effect relationships for all compounds are considered and analyzed by the Prism 3.0 program. $IC_{50}$ values, maximal effective concentrations, and reversibility are calculated and compared to amiloride and benzamil as positive controls.

Pharmacological Assays of Absorption (1) Apical Disappearance Assay

Bronchial cells (dog, human, sheep, or rodent cells) are seeded at a density of $0.25\times10^6/cm^2$ on a porous Transwell-Col collagen-coated membrane with a growth area of 1.13 $cm^2$ grown at an air-liquid interface in hormonally defined media that promotes a polarized epithelium. From 12 to 20 days after development of an air-liquid interface (ALI) the cultures are expected to be >90% ciliated, and mucins will accumulate on the cells. To ensure the integrity of primary airway epithelial cell preparations, the transepithelial resistance ($R_t$) and transepithelial potential differences (PD), which are indicators of the integrity of polarized nature of the culture, are measured. Human cell systems are preferred for studies of rates of absorption from apical surfaces. The disappearance assay is conducted under conditions that mimic the "thin" films in vivo (~25 µl) and is initiated by adding experimental sodium channel blockers or positive controls (amiloride, benzamil, phenamil) to the apical surface at an initial concentration of 10 µM. A series of samples (5 µl volume per sample) is collected at various time points, including 0, 5, 20, 40, 90 and 240 minutes. Concentrations are determined by measuring intrinsic fluorescence of each sodium channel blocker using a Fluorocount Microplate Fluorometer or HPLC. Quantitative analysis employs a standard curve generated from authentic reference standard materials of known concentration and purity. Data analysis of the rate of disappearance is performed using nonlinear regression, one phase exponential decay (Prism V 3.0).

2. Confocal Microscopy Assay of Amiloride Congener Uptake

Virtually all amiloride-like molecules fluoresce in the ultraviolet range. This property of these molecules may be used to directly measure cellular update using x-z confocal microscopy. Equimolar concentrations of experimental compounds and positive controls including amiloride and compounds that demonstrate rapid uptake into the cellular compartment (benzamil and phenamil) are placed on the apical surface of airway cultures on the stage of the confocal microscope. Serial x-z images are obtained with time and the magnitude of fluorescence accumulating in the cellular compartment is quantitated and plotted as a change in fluorescence versus time.

3. In Vitro Assays of Compound Metabolism

Airway epithelial cells have the capacity to metabolize drugs during the process of transepithelial absorption. Further, although less likely, it is possible that drugs can be metabolized on airway epithelial surfaces by specific ectoenzyme activities. Perhaps more likely as an ecto-surface event, compounds may be metabolized by the infected secretions that occupy the airway lumens of patients with lung disease, e.g. cystic fibrosis. Thus, a series of assays is performed to characterize the compound metabolism that results from the interaction of test compounds with human airway epithelia and/or human airway epithelial lumenal products.

In the first series of assays, the interaction of test compounds in KBR as an "ASL" stimulant are applied to the apical surface of human airway epithelial cells grown in the T-Col insert system. For most compounds, metabolism (generation of new species) is tested for using high performance liquid chromatography (HPLC) to resolve chemical species and the endogenous fluorescence properties of these compounds to estimate the relative quantities of test compound and novel metabolites. For a typical assay, a test solution (25 μl KBR, containing 10 μM test compound) is placed on the epithelial lumenal surface. Sequential 5 to 10 μl samples are obtained from the lumenal and serosal compartments for HPLC analysis of (1) the mass of test compound permeating from the lumenal to serosal bath and (2) the potential formation of metabolites from the parent compound. In instances where the fluorescence properties of the test molecule are not adequate for such characterizations, radiolabeled compounds are used for these assays. From the HPLC data, the rate of disappearance and/or formation of novel metabolite compounds on the lumenal surface and the appearance of test compound and/or novel metabolite in the basolateral solution is quantitated. The data relating the chromatographic mobility of potential novel metabolites with reference to the parent compound are also quantitated.

To analyze the potential metabolism of test compounds by CF sputum, a "representative" mixture of expectorated CF sputum obtained from 10 CF patients (under IRB approval) has been collected. The sputum has been be solubilized in a 1:5 mixture of KBR solution with vigorous vortexing, following which the mixture was split into a "neat" sputum aliquot and an aliquot subjected to ultracentrifugation so that a "supernatant" aliquot was obtained (neat=cellular; supernatant=liquid phase). Typical studies of compound metabolism by CF sputum involve the addition of known masses of test compound to "neat" CF sputum and aliquots of CF sputum "supernatant" incubated at 37° C., followed by sequential sampling of aliquots from each sputum type for characterization of compound stability/metabolism by HPLC analysis as described above. As above, analysis of compound disappearance, rates of formation of novel metabolites, and HPLC mobilities of novel metabolites are then performed.

4. Pharmacological Effects and Mechanism of Action of the Drug n Animals

The effect of compounds for enhancing mucociliary clearance (MCC) can be measured using an in vivo model described by Sabater et al., *Journal of Applied Physiology*, 1999, pp. 2191-2196, incorporated herein by reference.

EXAMPLES

Having generally described this invention, a further understanding can be obtained by reference to certain specific examples which are provided herein for purposes of illustration only and are not intended to be limiting unless otherwise specified.

Preparation of Sodium Channel Blockers

Materials and methods. All reagents and solvents were purchased from Aldrich Chemical Corp. and used without further purification. NMR spectra were obtained on either a Bruker WM 360 ($^1$H NMR at 360 MHz and $^{13}$C NMR at 90 MHz) or a Bruker AC 300 ($^1$H NMR at 300 MHz and $^{13}$C NMR at 75 MHz). Flash chromatography was performed on a Flash Elute™ system from Elution Solution (PO Box 5147, Charlottesville, Va. 22905) charged with a 90 g silica gel cartridge (40M FSO-0110-040155, 32-63 μm) at 20 psi ($N_2$). GC-analysis was performed on a Shimadzu GC-17 equipped with a Heliflex Capillary Column (Alltech); Phase: AT-1, Length: 10 meters, ID: 0.53 mm, Film: 0.25 micrometers. GC Parameters: Injector at 320° C., Detector at 320° C., FID gas flow: $H_2$ at 40 ml/min., Air at 400 ml/min. Carrier gas: Split Ratio 16:1, $N_2$ flow at 15 ml/min., $N_2$ velocity at 18 cm/sec. The temperature program is 70° C. for 0-3 min, 70-300° C. from 3-10 min, 300° C. from 10-15 mm.

HPLC analysis was performed on a Gilson 322 Pump, detector U/Vis-156 at 360 nm, equipped with a Microsorb MV C8 column, 100 A, 25 cm. Mobile phase: A=acetonitrile with 0.1% TFA, B=water with 0.1% TFA. Gradient program: 95:5 B:A for 1 min, then to 20:80 B:A over 7 min, then to 100% A over 1 min, followed by washout with 100% A for 11 min, flow rate: 1 ml/min.

Example 1

4-{4-[N-(3,5-diamino-6-chloropyrazine-2-carbonyl) guanidino]butyl}-N-(2-aminoethyl)benzamide hydrochloride (11698)

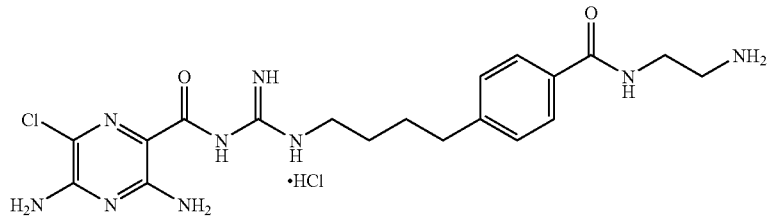

4-(4-Aminobutyl)benzoic acid (30)

A solution of sodium hydroxide (0.69 g, 17.37 mmol) in water (30 mL) was added to a solution of 24 (1.2 g, 5.79 mmol) in methanol (30 mL) and stirred at room temperature for 48 h. Then the solvent was removed under reduced pressure. Water (20 mL) was added and pH was adjusted to 7 with HCl. The white solid precipitate was filtered off, washed with water and dried in vacuum. The crude product 30 (1.39 g) was obtained as a white solid and used for the next step without further purification.

4-(4-Benzyloxycarbonylaminobutyl)benzoic acid (31)

Sodium hydrogencarbonate (0.95 g, 11.32 mmol) was added into a suspension of 30 in THF (120 mL), followed by water (10 mL), affording a clear solution. Benzyl chloroformate (1.21 mL, 8.49 mmol) was then added into the reaction mixture at 0° C. The reaction mixture was then stirred at room temperature overnight. After that, the solvent was removed under reduced pressure. Ethyl acetate (70 mL) was added to the residue and the solution was washed with 2N HCl (2×30 mL) and water (2×50 mL), then dried in vacuum. 1.82 g (98%) of 31 was obtained as a white solid. $^1$H NMR (300 MHz, DMSO-$d_6$) δ 1.11 (m, 2H), 1.28 (m, 2H), 2.33 (m, 2H), 3.02 (m, 2H), 5.01 (m, 2H), 7.15 (m, 7H), 7.93 (d 2H).

4-[4-(2-tert-Butoxycarbonylaminoethylcarbamoyl)phenyl]butyl}carbamic acid benzyl ester (32)

N,N'-Dicyclohexylcarbodiimide (DCC) (0.69 g, 3.36 mmol) was added to a cold (0° C.) methylene chloride solution of 31 (1 g, 3.05 mmol) and 1-hydroxybenzotriazole (HOBt) (0.41 g, 3.05 mmol) under a nitrogen atmosphere. The reaction mixture was then stirred at room temperature overnight. A white precipitate was formed. The solvent was removed under reduced pressure and the residue was separated by Flash™ (BIOTAGE, Inc) (90 g silica gel cartridge 40M, 3:2 methylene chloride/ethyl acetate) to provide 32 (0.9 g, 63%) as a white solid. $^1$H NMR (300 MHz, DMSO-$d_6$) δ 1.70 (m, 11H), 1.94 (m, 2H), 3.23 (m, 2H), 3.72 (m, 2H), 3.82 (m, 2H), 4.08 (m, 2H), 6.19 (s, 2H), 8.61 (m, 1H), 9.04 (m, 7H), 9.61 (d, 2H).

{2-[4-(4-Aminobutyl)benzoylamino]ethyl}carbamic acid tert-butyl ester (33)

A suspension of 32 (0.9 g, 1.92 mmol) with 10% palladium on carbon (0.30 g, wet) in methanol (50 mL) was stirred for 2 h at room temperature under atmospheric pressure of hydrogen. The mixture was then filtered through a silica gel pad. The solvent was evaporated and the residue was purified by Flash™ (BIOTAGE, Inc) (90 g silica gel cartridge 40M, 6:1:0.1 chloroform/ethanol/concentrated ammonium hydroxide) to provide 33 (0.405 g, 63%) as a white solid. $^1$H NMR (300 MHz, DMSO-$d_6$) δ 1.08 (m, 2H), 1.37 (s, 9H), 1.58 (m, 2H), 2.52 (m, 2H), 3.28 (m, 2H), 6.91 (m, 1H), 7.27 (d, 2H), 7.74 (d, 2H), 8.39 (m, 1H).

[2-(4-{4-[N'-(3,5-Diamino-6-chloropyrazine-2-carbonyl)guanidino]butyl}-benzoylamino)ethyl]carbamic acid tert-butyl ester (34)

1-(3,5-Diamino-6-chloropyrazinoyl)-2-methylisothiourea hydroiodide (0.32 g, 0.82 mmol) and triethylamine (0.27 mL, 1.64 mmol) were sequentially added into a solution of 33 (0.39 g, 0.82 mmol) in 5 mL of methanol. The reaction mixture was stirred in the boiling solvent for 2 h. The solvent was evaporated and the residue was separated by Flash™ (BIOTAGE, Inc) (90 g silica gel cartridge 40M, 6:1:0.1 chloroform/ethanol/concentrated ammonium hydroxide) to provide 34 (0.39 g, 62%) as a yellow solid. $^1$H NMR (300 MHz, DMSO-$d_6$) δ 1.07 (t, 2H), 1.38 (s, 9H), 1.52 (m, 2H), 1.65 (m, 2H), 2.66 (m, 2H), 3.10 (m, 2H), 3.28 (m, 2H), 4.39 (m, 1H), 6.65 (br s, 1H), 6.94 (m, 1H), 7.28 (m, 2H), 7.75 (d, 2H), 8.49 (m, 1H). m/z (APCI)=548 $[C_{24}H_{34}ClN_9O_4+H]^+$.

N-(2-Aminoethyl)-4-{4-[N'-(3,5-diamino-6-chloropyrazine-2-carbonyl)guanidino]butyl}-benzamide hydrochloride (35 (11698))

The solution of 34 (0.104 g, 0.19 mmol) in a mixture of methanol/HCl (1:1, 8 mL) was stirred at room temperature for 0.5 h; then the solvent was completely evaporated, affording 0.099 g (100%) of 35 as a yellow solid. $^1$H NMR (300 MHz, DMSO-$d_6$) δ 1.60 (m, 4H), 2.69 (m, 2H), 2.98 (m, 2H), 3.33 (m, 2H), 3.52 (m, 2H), 7.32 (d, 2H), 7.90 (d, 2H), 8.23 (br s, 2H), 8.82 (m, 1H), 8.90 (br s, 1H), 9.02 (br s, 1H), 9.37 (m, 1H), 10.57 (s, 1H). m/z (APCI)=448 $[C_{19}H_{26}ClN_9O_2+H]^+$.

Example 2

4-{4-[N'-(3,5-diamino-6-chloropyrazine-2-carbonyl)guanidino]butyl}-N-(2-guanidinoethyl)benzamide hydrochloride (11834)

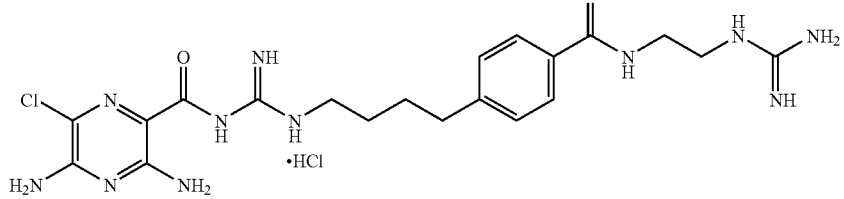

4-{4-[N'-(3,5-Diamino-6-chloropyrazine-2-carbonyl)guanidino]butyl}-N-[2-N'',N'''-di-(butyloxycarbonylguanidino-ethyl]benzamide (36)

Triethylamine (0.34 mL, 2.44 mmol) was added into a suspension of 35 in methanol (25 mL). The reaction mixture was stirred at room temperature for 20 min; at which time the suspension became a clear solution. N,N'-di-(tert-butoxycarbonyl)-N''-trifluoromethanesulfonylguanidine (Goodman's reagent) (0.193 g, 0.489 mmol) was added into the reaction. The reaction mixture was stirred at room temperature for additional 6 h, after that the solvent was removed under reduced pressure and the residue was purified by Flash™ (BIOTAGE, Inc) (90 g silica gel cartridge 40M, 6:1:0.1 chloroform/ethanol/concentrated ammonium hydroxide) to provide 36 (0.18 g, 80%) as a yellow solid. $^1$H NMR (300 MHz, DMSO-d$_6$) δ 1.40 (s, 9H), 1.47 (s, 9H), 1.52 (m, 2H), 1.65 (m, 2H), 2.68 (m, 2H), 3.18 (br s, 2H), 3.40 (m, 2H), 3.49 (m, 2H), 6.77 (br s, 2H), 7.30 (d, 2H), 7.75 (d, 2H), 8.50 (br s, 2H).

4-{4-[N'-(3,5-Diamino-6-chloropyrazine-2-carbonyl)guanidino]butyl}-N-(2-guanidino-ethyl)benzamide hydrochloride (37 (11834))

The solution of 36 (0.155 g, 0.22 mmol) in a mixture of methanol/HCl (1:1, 4 mL) was stirred at room temperature for 2 h, then the solvent was evaporated and the residue dried in vacuum to provide 0.126 g (100%) of 37 as a yellow solid. $^1$H NMR (300 MHz, DMSO-d$_6$) δ 1.54 (m, 2H), 1.65 (m, 2H), 2.68 (m, 2H), 3.35 (br.s, 4H), 7.32 (d, 2H), 7.90 (d, 2H), 8.79 (m, 1H), 8.92 (br s, 1H), 8.90 (br s, 1H), 9.02 (br s, 1H), 9.37 (m, 1H), 10.57 (s, 1H). m/z (APCI)=490 [C$_{20}$H$_{28}$ClN$_{11}$O$_2$+H]$^+$.

Example 3

N-(3,5-diamino-6-chloropyrazine-2-carbonyl)-N'-{4-[4-(3-guanidino-2-hydroxypropoxy)phenyl]butyl}guanidine hydrochloride (11975)

{4-[4-(3-Amino-2-hydroxypropoxy)phenyl]butyl}carbamic acid benzyl ester (40)

An ethanol solution of 39 (0.86 g, 2.42 mmol) was saturated with ammonia and stirred overnight at room temperature. The solvent was evaporated and the residue was purified by Flash™ (BIOTAGE, Inc) (90 g silica gel cartridge 40M, 6:1:0.1 chloroform/ethanol/concentrated ammonium hydroxide) to provide 40 (0.75 g, 87%) as a white solid. $^1$H NMR (300 MHz, DMSO-d$_6$) δ 1.40 (m, 2H), 1.51 (m, 2H), 2.50 (m, 2H), 2.58 (m, 1H), 2.68 (m, 1H), 3.00 (m, 2H), 3.69 (m, 1H), 3.80 (m, 1H), 3.90 (m, 1H), 5.08 (s, 2H), 6.82 (d, 2H), 7.06 (d, 2H), 7.35 (br s, 5H).

{4-[4-(3-tert-Butoxycarbonylamino-2-hydroxypropoxy)-phenyl]butyl}carbamic acid tert-butyl ester (41)

The compound 41 was prepared in a similar manner to the synthesis of compound 25, starting from compound 40 (0.75 g, 2.03 mmol). It was purified by Flash™ (BIOTAGE, Inc) (90 g silica gel cartridge 40M, 2:1 hexane/ethyl acetate) as a white solid (0.8 g, 83%). $^1$H NMR (300 MHz, CDCl$_3$) δ 1.45 (s, 9H), 1.57 (m, 4H), 2.58 (m, 2H), 3.20 (m, 2H), 3.31 (m, 2H), 3.94 (m, 2H), 4.10 (m, 1H), 4.73 (br s, 1H), 5.00 (br s, 1H), 5.10 (s, 2H), 6.81 (d, 2H), 7.06 (d, 2H), 7.35 (br s, 5H).

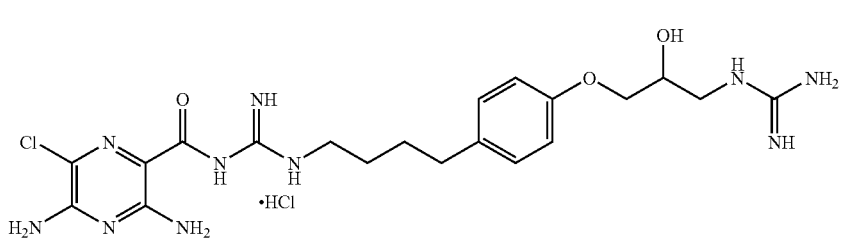

11975

The synthesis of [4-(4-allyloxyphenyl)butyl]carbamic acid benzyl ester (38) was described in the previously provided experimental details (as compound 30).

[4-(4-Oxiranylmethoxyphenyl)butyl]carbamic acid benzyl ester (39)

3-Chloro-peroxybenzoic acid (2.46 g, 14.25 mmol) was added into a methylene chloride solution (100 mL) of 38 (1.86 g, 5.48 mmol), and the reaction was stirred at room temperature overnight. After that, the solvent was removed under reduced pressure and the residue was purified by flash chromatography (silica gel, 8:1:1 methylene chloride/hexane/ethyl acetate). To eliminate the admixture of benzoic acid the methylene chloride solution of the product was sequentially washed with a saturated aqueous solution of sodium hydrogen carbonate and water, then dried over anhydrous sodium sulfate and evaporated to provide 1.4 g (72%) of 39 as a yellow solid. $^1$H NMR (300 MHz, CDCl$_3$) δ 1.57 (m, 4H), 2.56 (m, 2H), 2.78 (m, 1H), 2.91 (m, 1H), 3.21 (m, 2H), 3.36 (m, 1H), 3.97 (m, 1H), 4.19 (m, 1H), 5.08 (s, 2H), 6.82 (d, 2H), 7.06 (d, 2H), 7.72 (s, 5H).

{3-[4-(4-Aminobutyl)phenoxy]-2-hydroxypropyl}carbamic acid tert-butyl ester (42)

A suspension of 41 (0.8 g, 1.69 mmol) with 10% palladium on carbon (0.40 g, wet) in methanol (30 mL) was stirred for 3 h at room temperature under atmospheric pressure of hydrogen. The mixture was then filtered through a silica gel pad; the solvent was evaporated to provide 42 (0.705 g, 99%) as a white solid. $^1$H NMR (300 MHz, CDCl$_3$) δ 1.45 (s, 9H), 1.55 (m, 4H), 2.58 (m, 4H), 2.71 (m, 2H), 3.29 (m, 1H), 3.45 (m, 2H), 3.92 (m, 2H), 4.10 (br s, 1H), 5.10 (br s, 1H), 6.81 (d, 2H), 7.08 (d, 2H).

[3-(4-{4-[N'-(3,5-Diamino-6-chloropyrazine-2-carbonyl)guanidino]butyl}phenoxy)-2-hydroxypropyl]carbamic acid tert-butyl ester (43)

Compound 43 was prepared in a similar manner to the synthesis of compound 29, starting from compound 42 (0.46 g, 1.36 mmol). It was purified by Flash™ (BIOTAGE, Inc) (90 g silica gel cartridge 40M, 6:1:0.1 chloroform/ethanol/ concentrated ammonium hydroxide) as a yellow solid (0.37 g, 57%). $^1$H NMR (300 MHz, DMSO-d$_6$) δ 1.38 (s, 9H), 1.58 (br s, 4H), 2.55 (m, 2H), 3.00 (m, 2H), 3.08 (m, 2H), 3.33 (m, 2H), 3.82 (m, 3H), 5.13 (br s, 1H), 6.85 (d, 2H), 7.10 (d, 2H), 7.46 (br s, 2H).

N-{4-[4-(4-Amino-2-hydroxypropoxy)phenyl]butyl}-N'-(3,5-diamino-6-chloropyrazine-2-carbonyl) guanidine (44)

The free base of compound 44 was prepared in a similar manner to the synthesis of the compound 28, starting from the compound 43 (0.18 g, 0.33 mmol) and purified by Flash™ (BIOTAGE, Inc) (90 g silica gel cartridge 40M, 2:1:0.1 chloroform/ethanol/concentrated ammonium hydroxide) to afford the product free base as a yellow solid. It was then treated with 3% HCl. The solvent was evaporated, and the residue was dried in vacuum to afford 0.125 g (73%) of the compound 44. $^1$H NMR (300 MHz, DMSO-d$_6$) δ 1.58 (br s, 4H), 2.55 (m, 2H), 2.84 (br s, 1H), 3.03 (br s, 1H), 3.34 (br s, 2H), 3.94 (m, 2H), 5.13 (br s, 1H), 6.85 (d, 2H), 7.13 (d, 2H), 8.13 (br s, 2H), 8.90 (br s, 1H), 9.00 (br s, 1H), 9.34 (br s, 1H), 10.56 (s, 1H).

N-(3,5-Diamino-6-chloro-pyrazine-2-carbonyl)-N'-{4-[4-(3-(N'',N'''-di-tert-butyl-oxycarbonyl)-guanidino)-2-hydroxy-propoxy)phenyl]-butyl}-guanidine (45)

Triethylamine (0.30 mL, 2.14 mmol) was added into a solution of 44 in methanol (10 mL) followed by the addition of N,N'-di-(tert-butoxycarbonyl)-N''-trifluoromethanesulfonylguanidine (Goodman's reagent) (0.169 g, 0.4295 mmol). The reaction mixture was stirred at room temperature for 2 h. After that the solvent was removed under reduced pressure and the residue was purified by Flash™ (BIOTAGE, Inc) (90 g silica gel cartridge 40M, 6:1:0.1 chloroform/ethanol/concentrated ammonium hydroxide) to provide 45 (0.154 g, 78%) as a yellow solid. $^1$H NMR (300 MHz, CD$_3$OD) δ 1.47 (s, 9H), 1.52 (s, 9H), 1.66 (br s, 4H), 2.58 (m, 2H), 3.23 (br s, 2H), 3.48 (m, 1H), 3.70 (m, 1H), 3.95 (m, 2H), 4.09 (m, 1H), 6.88 (d, 2H), 7.10 (d, 2H).

N-(3,5-Diamino-6-chloropyrazine-2-carbonyl)-N'-{4-[4-(3-guanidino-2-hydroxypropoxy)phenyl]butyl}guanidine hydrochloride (46)

A solution of 45 (0.134 g, 0.19 mmol) in concentrated hydrochloric acid was stirred at room temperature for 0.5 h. The solvent was then evaporated and the residue dried in vacuum to provide 0.108 g (99%) of 46 as a yellow solid. $^1$H NMR (300 MHz, DMSO-d$_6$) δ 1.60 (br s, 4H), 2.52 (br s, 1H), 3.28 (m, 1H), 3.36 (m, 2H), 4.91 (s, 2H), 6.88 (d, 2H), 7.12 (d, 2H), 7.79 (m, 1H), 8.92 (br s, 1H), 9.03 (br s, 1H), 9.37 (m, 1H), 10.57 (s, 1H). m/z (APCI)=493 [C$_{20}$H$_{29}$ClN$_{10}$O$_3$+H]$^+$.

Example 4

N-(3,5-Diamino-6-chloropyrazine-2-carbonyl)-N'-[4-(4-bis(methanesulfonyl)aminophenyl)butyl]guanidine (10316)

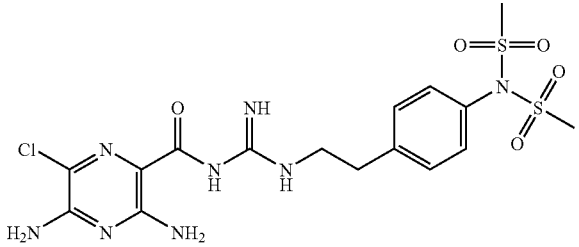

10316

[4-(4-Nitrophenyl)but-3-ynyl]carbamic acid tert-butyl ester (51)

To a mixture of anhydrous THF and triethylamine (20 mL, 1/1) were sequentially added 1-iodo-4-nitrobenzene (2.0 g, 8.032 mmol) and copper(I)iodide (0.31 g, 1.606 mmol). The mixture was stirred at room temperature for 15 min. The flask was evacuated and re-filled with argon four times to ensure no oxygen remained. The catalyst, dichlorobis(triphenylphosphine)-palladium(II) (0.56 g, 0.803 mmol) was added into the mixture under argon protection, followed by dropwise addition of but-3-ynyl-carbamic acid tert-butyl ester (1.62 g, 9-638 mmol). The newly formed reaction mixture was further stirred at room temperature overnight. The solid in the reaction mixture was vacuum filtered. The filtrate was concentrated. The residue was re-dissolved in methylene chloride and purified by column chromatography, eluting with a mixture of ethyl acetate (0-10%) and hexanes (100-90%) to afford 2.08 g (89%) of the product 51 as an orange solid. $^1$H NMR (CDCl$_3$) δ 1.46 (s, 9H), 2.66 (t, J=6.5 Hz, 2H), 3.36-3.43 (m, 2H), 4.86 (br s, 1H), 7.53 (d, J=8.7 Hz, 2H), 8.16 (d, J=8.7 Hz, 2H). m/z (APCI)=291 [Cl$_5$H$_{18}$N$_2$O$_4$+H]$^+$, 191 [Cl$_5$H$_{18}$N$_2$O$_4$–Boc+H]$^+$.

[4-(4-Aminophenyl)butyl]carbamic acid tert-butyl ester (52)

To a solution of compound 51 (2.01 g, 6.923 mmol) in ethanol (50 mL) was added 10% palladium on carbon (737 mg, wet) in one portion under argon protection. The flask was evacuated and re-filled with argon three times (to remove oxygen), and the mixture stirred at room temperature overnight under one atmosphere of hydrogen. The reaction system was then purged with nitrogen, and the catalyst was vacuum filtered and washed with ethanol (2×5 mL). The filtrate and washings were combined and concentrated under reduced pressure. The residue was chromatographed over silica gel, eluting with a mixture of ethyl acetate (0-25%) and hexanes (100-75%), to afford 1.75 g (96%) of the product 52 as a colorless viscous oil. $^1$H NMR (CDCl$_3$) δ 1.44 (s, 9H), 1.47-1.64 (m, 4H), 2.50 (t, J=7.1 Hz, 2H), 3.08-3.14 (m, 2H), 3.57 (br s, 2H), 4.55 (br s, 1H), 6.62 (d, J=8.2 Hz, 2H), 6.95 (d, J=8.2 Hz, 2H). m/z (APCI)=265 [C$_{15}$H$_{24}$N$_2$O$_2$+H]$^+$.

4-{4-[Bis(methanesulfonyl)amino]phenyl}butylcarbamic acid tert-butyl ester (53)

Compound 52 (0.16 g, 0.605 mmol) was dissolved in anhydrous THF (5 mL). To the clear solution were sequentially added triethylamine (0.18 mL, 1.21 mmol) and 4-dimethylaminopyridine (15 mg, 0.121 mmol). The mixture was cooled to about −10° C. for 15 min by a methanol-ice bath. To the cold solution was slowly added methanesulfonyl chloride (51 µL). The solution was further stirred at the temperature (about −10° C.) for an additional 30 min, then allowed to slowly warm up to room temperature by removing the cooling bath. The reaction mixture was concentrated under reduced pressure. The residue was chromatographed over silica gel, eluting with a mixture of ethyl acetate (0-35%) and hexanes (100-65%), to afford 0.212 g (83%) of the product 53 as a white solid. $^1$H NMR (CDCl$_3$) δ 1.44 (s, 9H), 1.52-1.70 (m, 4H), 2.68 (t, J=7.4 Hz, 2H), 3.13-3.18 (m, 2H), 3.40 (s, 6H), 4.53 (br s, 1H), 7.27 (s, 4H). m/z (APCI)=321 [$C_{17}H_{28}N_2O_6S_2$−Boc+H]$^+$.

4-[4-Bis(methanesulfonyl)amino)phenyl]butylamine (54)

A solution of compound 53 (0.21 g, 0.499 mmol) dissolved in methylene chloride (10 mL) was treated with trifluoroacetic acid (1 mL) at room temperature for 2 hours, then concentrated under vacuum. The residue was taken into methanol (2 mL), and concentrated again under reduced pressure. The procedure was repeated three times to ensure no residual trifluoroacetic acid remained. The product was completely dried under vacuum, and directly used for the next reaction without further purification. 0.196 g (100%) of the compound 54 was obtained as a colorless viscous oil. $^1$H NMR (DMSO-d$_6$) δ 1.50-1.72 (m, 4H), 2.65 (t, J=7.4 Hz, 2H), 2.84-2.89 (m, 2H), 3.51 (s, 6H), 7.33 (d, J=8.3 Hz, 2H), 7.42 (d, J=8.3 Hz, 2H). m/z (APCI)=321 [$C_{12}H_{20}N_2O_4S_2$+H]$^+$.

N-(3,5-Diamino-6-chloropyrazine-2-carbonyl)-N'-[4-(4-bis(methanesulfonyl)-aminophenyl)butyl]guanidine (55, 10316)

Compound 54 (0.095 g, 0.296 mmol) was mixed with ethanol (5 mL). The mixture was heated at 65° C. for 15 min to achieve complete dissolution. To the clear solution were sequentially added diisopropylethylamine (0.26 mL, 1.48 mmol) and 1-(3,5-diamino-6-chloropyrazinoyl)-2-methylisothiourea hydroiodide (0.127 g, 0.326 mmol). The mixture was heated at the same temperature for an additional 1.5 hours, and subsequently concentrated under vacuum. The residue was chromatographed over silica gel, eluting with a mixture of concentrated ammonium hydroxide (0-1%), methanol (0-10%), and methylene chloride (100-89%), to afford 0.113 g (72%) of the product 55 as a light yellow solid. mp 174-176° C. (decomposed). $^1$H NMR (DMSO-d$_6$) δ 1.48-1.68 (m, 4H), 2.64-2.69 (m, 2H), 3.12-3.25 (m, 2H), 3.51 (s, 6H), 6.65-6.78 (br s, 3H), 7.31 (d, J=8.2 Hz, 2H), 7.41 (d, J=8.2 Hz, 2H), 9.05 (br s, 2H). m/z (APCI)=533 [$C_{18}H_{25}ClN_8O_5S_2$+H]$^+$.

Example 5

N-(3,5-diamino-6-chloropyrazine-2-carbonyl)-N'-{4-[4-(2-chlorotrimethylammonium)ethoxyphenyl]butyl}guanidine hydrochloride (11223)

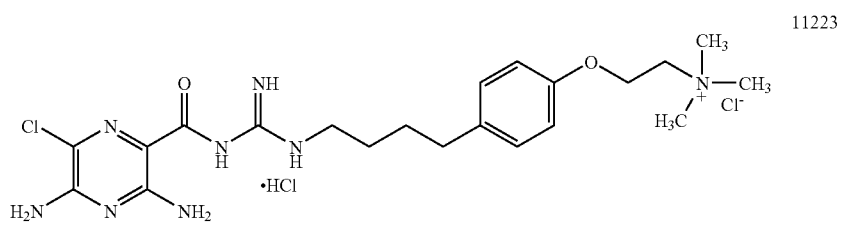

{4-[4-(2-Dimethylaminoethoxy)phenyl]butyl}carbamic acid benzyl ester (62)

A mixture of [4-(4-hydroxyphenyl)butyl]carbamic acid benzyl ester (1.5 g, 5 mmol), 2-dimethylaminochloroethane hydrochloride (1.4 g, 10 mmol), potassium carbonate (2.76 g, 20 mmol) and 18-crown-6 ether (154 mg, 0.58 mmol) was stirred at 80° C. (oil bath) for 18 h. After this time, the solvent was removed under reduced pressure and the residue was purified by Flash™ (BIOTAGE, Inc) (90 g silica gel cartridge 40M, 10:1:0.1 chloroform/methanol/concentrated ammonium hydroxide) to provide 62 (1.1 g, 61%) as a white solid. $^1$H NMR (300 MHz, CDCl$_3$) δ 1.56 (m, 4H), 2.32 (s, 6H), 2.56 (m, 2H), 2.71 (t, 2H), 3.18 (m, 2H), 4.04 (t, 2H), 4.78 (br s, 1H), 5.08 (s, 2H), 6.83 (d, 2H), 7.06 (d, 2H), 7.35 (m, 5H).

4-[4-(2-Dimethylaminoethoxy)phenyl]butylamine (63)

The protected amine 62 (0.552 g, 1.5 mmol) was stirred with 10% palladium on carbon (0.127 g, wet) in methanol (50 mL) at room temperature for 3.5 h under hydrogen (1 atm). After this time, the catalyst was filtered off and the solvent was removed under reduced pressure to give the free amine 63 (0.27 g, 77%) as a white powder. $^1$H NMR (300 MHz, CD$_3$OD) δ 1.55 (m, 4H), 2.32 (s, 6H), 2.54 (m, 2H), 2.75 (m, 2H), 4.02 (m, 2H), 6.78 (d, 2H), 7.08 (d, 2H).

1-tert-Butyloxycarbonyl-3-(3,5-diamino-6-chloropyrazine-2-carbonyl)-2-methyl-isothiourea (64)

4-Dimethylaminopyridine (87 mg, 0.7 mmol) was added to a stirring solution of di-tert-butyl dicarbonate (0.8 g, 3.6 mmol) and 1-(3,5-diamino-6-chloropyrazinoyl)-2-methyl-isothiourea hydroiodide (1.14 g, 0.5 mmol) in THF/triethylamine (62 mL, 30/1). The reaction mixture was then stirred at room temperature for 48 h. After this time, the solvent was removed under reduced pressure. The residue was purified by flash chromatography (silica gel, 1:1 ethyl acetate/hexanes) to give the protected isothiourea 64 (0.34 g, 32%) as a yellow powder. $^1$H NMR (300 MHz, DMSO-d$_6$) δ 1.51 (s, 9H), 2.30 (s, 3H), 7.40 (br s, 4H).

N-tert-Butyloxycarbonyl-N'-(3,5-diamino-6-chloro-pyrazine-2-carbonyl)-N"-{4-[4-(2-dimethylaminoethoxy)phenyl]butyl}guanidine (65)

A suspension of compound 63 (0.22 g, 0.93 mmol) and 64 (0.33 g, 0.92 mmol) in THF/triethylamine (11 mL, 10/1) was stirred at room temperature for 48 h. After this time, a clear solution was formed. The solvent was removed under reduced pressure and the residue was purified by flash chromatography (silica gel, 10:1:0.1 chloroform/methanol/concentrated ammonium hydroxide) to provide the guanidine 65 (0.3 g, 60%) as a yellow solid. $^1$H NMR (300 MHz, DMSO-$d_6$) δ 1.42 (s, 9H), 1.55 (m, 4H), 2.19 (s, 6H), 2.58 (m, 4H), 3.99 (m, 2H), 6.83 (d, 2H), 7.12 (d, 2H), 7.40 (br s, 2H), 9.02 (m, 2H).

N-tert-Butyloxycarbonyl-N'-(3,5-diamino-6-chloro-pyrazine-2-carbonyl)-N"-{4-[4-(2-iodotrimethylammoniumethoxy)phenyl]butyl}guanidine (66)

Iodomethane (30 μL, 0.49 mmol) was added to a suspension of 65 (0.29 g, 0.52 mmol) in THF (50 mL). The mixture was stirred at room temperature overnight. After this time, additional THF (7 mL) was added and stirring was continued for 2 d to give a clear solution. The solvent from the resulting solution was removed under reduced pressure. The residue was washed with THF (2×5 mL) and dried to afford the salt 66 (0.22 g, 32%) as a yellow powder. $^1$H NMR (300 MHz, DMSO-$d_6$) δ 1.42 (s, 9H), 1.56 (m, 4H), 2.58 (m, 2H), 3.15 (s, 9H), 3.75 (m, 2H), 4.42 (m, 2H), 6.92 (d, 2H), 7.18 (d, 2H), 7.36 (br s, 2H), 9.02 (m, 1H).

[2-(4-{4-[N'-(3,5-Diamino-6-chloropyrazine-2-carbonyl)guanidino]butyl}phenoxy)ethyl]-trimethylammonium chloride (67, 11223)

Trifluoroacetic acid (2 mL) was added to the protected guanidine 66 (0.092 g, 0.13 mmol). The reaction mixture was stirred at room temperature for 15 min. The solvent was removed under reduced pressure and the residue was washed with ethyl acetate (2×1 mL) and dried in vacuum. The obtained dry solid was treated with an aqueous solution of ammonium hydroxide (15%, 1 mL). The formed precipitate was collected by centrifugation and washed with cold water (1 mL). The remaining solid was dissolved in 10% hydrochloric acid, and the solvent was then removed under reduced pressure. The resulting yellow solid was dried in vacuum to give compound 67 (0.055 g, 82%). $^1$H NMR (300 MHz, CD$_3$OD) δ 1.68 (br s, 4H), 2.65 (m, 2H), 3.35 (m, 2H), 3.83 (m, 2H), 4.46 (m, 2H), 4.95 (s, 9H), 6.96 (d, 2H), 7.18 (d, 2H), 9.25 (br s, 1H). m/z (APCI)=499 [C$_{21}$H$_{32}$Cl$_2$N$_8$O$_2$+H]$^+$.

Sodium Channel Blocking Activity

The compounds shown in the Tables below were tested for potency in canine bronchial epithelia using the in vitro assay described above. Amiloride was also tested in this assay as a positive control. The results for the compounds of the present invention are reported as fold-enhancement values relative to amiloride.

Example 6

| X= | Y= | Fold Amiloride* |
|---|---|---|
| —NHCO$_2$+ | —CO$_2$CH$_3$ | 2.4 ± 10 (5) |
| ‖‖NH$_2$ | —CO$_2$H | 17.2 ± 5.8 (4) |
| ‖‖NH$_2$ | —CO$_2$CH$_3$ | 21.1 ± 14.1 (2) |
| ‖‖‖‖NH$_2$ | —CONH$_2$ | |

*Relative potency for Amiloride = 665 nM.
**Relative potency for CF552 = 100 using IC$_{50}$ from 552 in same run.
***3$^{rd}$ Wash
(a) Old Database
(b) NA = Not Available
(c) 1 of 5 is high outlier (252)

Example 7

| X= | Fold Amiloride* |
|---|---|
| N(CH$_3$)$_2$ | 25.3 ± 2.3 (3) |
| N⊕(CH$_3$)$_3$ | 39.4 ± 0.3 (3) |

*Relative potency for Amiloride = 665 nM.
**Relative potency for CF552 = 100 using IC$_{50}$ from 552 in same run.
***3$^{rd}$ Wash
a Guanidinine is Acylated Example 8

| R=/Z= | O‖CNHCH$_2$CH$_2$R | NH(C=O)CH$_2$CH$_2$R |
|---|---|---|
| NH$_2$ Xamiloride | 86.2 ± 30.1 | 170 |

| R=/Z= | OH\|OCH$_2$CHCH$_2$R | O‖CNHCH$_2$CH$_2$R |
|---|---|---|
| NH‖—NHCNH$_2$ Xamiloride | 182.3 ± 106.3 (12) | 139.7 ± 62.4 |

References. 1. Rappoport, D. A.; Hassid, Z.; *J. Amer. Chem. Soc.*, 1951, 73, 5524-5525, incorporated herein by reference.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of increasing hydration of a mucosal surface of a subject, comprising topically administering to a mucosal surface of a subject an effective amount of a compound represented by formula (I):

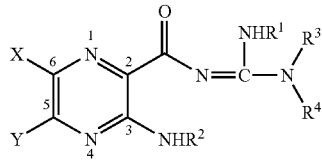

where
X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;
Y is hydrogen, hydroxyl, mercapto, lower alkoxy, lower alkyl-thio, halogen, lower alkyl, unsubstituted or substituted mononuclear aryl, or $-N(R^2)_2$;
$R^1$ is hydrogen or lower alkyl;
each $R^2$ is, independently, $-R^7$, $-(CH_2)_m-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)_n-C(=O)NR^7R^{10}$, $-(CH_2)_n-Z_g-R^7$, $-(CH_2)_m-NR^{10}-CH_2(CHOR^8)(CHOR^8)_n-CH_2OR^8$, $-(CH_2)_n-CO_2R^7$, or

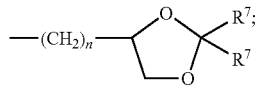

wherein when two $-CH_2OR^8$ groups are located 1,2- or 1,3- with respect to each other the $R^8$ groups may be joined to form a cyclic mono- or di-substituted 1,3-dioxane or 1,3-dioxolane;
$R^3$ and $R^4$ are each, independently, hydrogen, a group represented by formula (A), lower alkyl, hydroxy lower alkyl, phenyl, phenyl-lower alkyl, (halophenyl)-lower alkyl, lower-(alkylphenylalkyl), lower (alkoxyphenyl)-lower alkyl, naphthyl-lower alkyl, or pyridyl-lower alkyl, with the proviso that at least one of $R^3$ and $R^4$ is a group represented by formula (A):

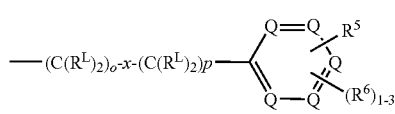

wherein
each $R^L$ is, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_n-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_2-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

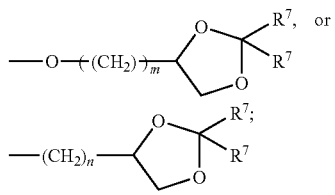

wherein when two $-CH_2OR^8$ groups are located 1,2- or 1,3- with respect to each other the $R^8$ groups may be joined to form a cyclic mono- or di-substituted 1,3-dioxane or 1,3-dioxolane;
each o is, independently, an integer from 0 to 10;
each p is an integer from 0 to 10;
with the proviso that the sum of o and p in each contiguous chain is from 1 to 10;
each x is, independently, O, $NR^{10}$, $C(=O)$, CHOH, $C(=N-R^{10})$, $CHNR^7R^{10}$, or represents a single bond;
each $R^5$ is, independently, $-(CH_2)_n-N(SO_2R^7)_2$, $-O-(CH_2)_m-N(SO_2R^7)_2$, $-(CH_2)_n-NR^{12}R^{12}$, $-O-(CH_2)_m-NR^{12}R^{12}$, $-O-(CH_2)_m-(Z)_gR^{12}$, $-(CH_2)_nNR^{11}R^{11}$, $-O-(CH_2)_mNR^{11}R^{11}$, $-(CH_2)_n-N^{\oplus}-(R^{11})_3$, $-O-(CH_2)_m-N^{\oplus}-(R^{11})_3$, $-(CH_2)_n-(Z)_g-(CH_2)_m-NR^{10}R^{10}$, $-O-(CH_2)_m-(Z)_g(CH_2)_m-NR^{10}R^{10}$, $-(CH_2CH_2O)_m-CH_2CH_2NR^{12}R^{12}$, $-O-(CH_2CH_2O)_m-CH_2CH_2NR^{12}R^{12}$, $-(CH_2)_n-(C=O)NR^{12}R^{12}$, $-O-(CH_2)_m-(C=O)NR^{12}R^{12}$, $-O-(CH_2)_m-(CHOR^8)_mCH_2NR^{10}-(Z)_g-R^{10}$, $-(CH_2)_n-(CHOR^8)_mCH_2-NR^{10}-(Z)_g-R^{10}$, $-(CH_2)_mNR^{10}-(CH_2)_m(CHOR^8)_nCH_2NR^{10}-(Z)_g-R^{10}$, $-O(CH_2)_m-NR^{10}-(CH_2)_m-(CHOR^8)_n CH_2NR^{10}-(Z)_g-R^{10}$, -(Het)-(CH_2)_m-OR^8, -(Het)-(CH_2)_m-NR^7R^{10}, -(Het)-(CH_2)_m(CHOR^8)(CHOR^8)_n-CH_2OR^8, -(Het)-(CH_2CH_2O)_m-R^8, -(Het)-(CH_2CH_2O)_m-CH_2CH_2NR^7R^{10}, -(Het)-(CH_2)_m-C(=O)NR^7R^{10}, -(Het)-(CH_2)_m-(Z)_g-R^7, -(Het)-(CH_2)_m-NR^{10}-CH_2(CHOR^8)(CHOR^8)_n-CH_2OR^8, -(Het)-(CH_2)_m-CO_2R^7, -(Het)-(CH_2)_m-NR^{12}R^{12}, -(Het)-(CH_2)_n-NR^{12}R^{12}, -(Het)-(CH_2)_m-(Z)_gR^{12}, -(Het)-(CH_2)_m NR^{11}R^{11}, -(Het)-(CH_2)_m-N^{\oplus}-(R^{11})_3, -(Het)-(CH_2)_m-(Z)_g-(CH_2)_m-NR^{10}R^{10}, -(Het)-(CH_2CH_2O)_m-CH_2CH_2NR^{12}R^{12}, -(Het)-(CH_2)_m-(C=O)NR^{12}R^{12}, -(Het)-(CH_2)_m-(CHOR^8)_m CH_2NR^{10}-(Z)_g-R^{10}, -(Het)-(CH_2)_m-NR^{10}-(CH_2)_m-(CHOR^8)_nCH_2NR^{10}-(Z)_g-R^{10}, $-C(=O)NH-(CH_2)_m-NH-C(=NH)-N(R^7)_2$, or $-NH-C(=O)-(CH_2)_mNH-C(=NH)-N(R^{10})_2$, wherein when two $-CH_2OR^8$ groups are located 1,2- or 1,3- with respect to each other the $R^8$ groups may be joined to form a cyclic mono- or di-substituted 1,3-dioxane or 1,3-dioxolane, $-(CH_2)_n(CHOR^8)(CHOR^8)_n-CH_2OR^8$, with the proviso that at least two $-CH_2OR^8$ are located adjacent to each other and the $R^8$ groups are joined to form a cyclic mono- or di-substituted 1,3-dioxane or 1,3-dioxolane, —O—(CH$_2$)$_m$(CHOR$^8$)(CHOR$^8$)$_n$—CH$_2$OR$^8$, with the proviso that at least two —CH$_2$OR$^8$ are located adjacent to each other and the R$^8$ groups are joined to form a cyclic mono- or di-substituted 1,3-dioxane or 1,3-dioxolane, —(CH$_2$)$_n$—NR$^{10}$—CH$_2$(CHOR$^8$)(CHOR$^8$)$_n$—CH$_2$OR$^8$, with the proviso that at least two —CH$_2$OR$^8$ are located adjacent to each other and the R$^8$ groups are joined to form a cyclic mono- or di-substituted 1,3-dioxane or 1,3-dioxolane, or —O—(CH$_2$)$_m$—NR$^{10}$—CH$_2$(CHOR$^8$)(CHOR$^8$)$_n$—CH$_2$OR$^8$, with the proviso that at least two —CH$_2$OR$^8$ are located adjacent to each other and the R$^8$ groups are joined to form a cyclic mono- or di-substituted 1,3-dioxane or 1,3-dioxolane;

each R$^6$ is, independently, —R$^5$, —R$^7$, —OR$^8$, —N(R$^7$)$_2$, —(CH$_2$)$_m$—OR$^8$, —O—(CH$_2$)$_m$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

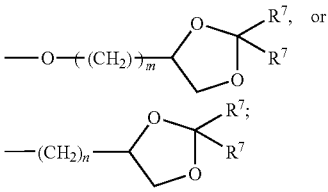

wherein when two R$^6$ are —OR$^{11}$ and are located adjacent to each other on a phenyl ring, the alkyl moieties of the two R$^6$ may be bonded together to form a methylenedioxy group, and wherein when two —CH$_2$OR$^8$ groups are located 1,2- or 1,3- with respect to each other the R$^8$ groups may be joined to form a cyclic mono- or di-substituted 1,3-dioxane or 1,3-dioxolane;

each R$^7$ is, independently, hydrogen or lower alkyl;

each R$^8$ is, independently, hydrogen, lower alkyl, —C(=O)—R$^1$, glucuronide, 2-tetrahydropyranyl, or

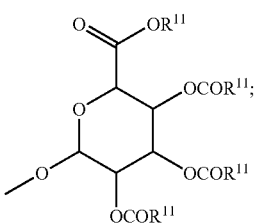

each R$^9$ is, independently, —CO$_2$R$^7$, —CON(R$^7$)$_2$, —SO$_2$CH$_3$, or —C(=O)R$^7$;

each R$^{10}$ is, independently, —H, —SO$_2$CH$_3$, —CO$_2$R$^7$, —C(=O)NR$^7$R$^9$, —C(=O)R$^7$, or —CH$_2$—(CHOH)$_n$—CH$_2$OH;

each Z is, independently, CHOH, C(=O), CHNR$^7$R$^{10}$, C=NR$^{10}$, or NR$^{10}$;

each R$^{11}$ is, independently, lower alkyl;

each R$^{12}$ is independently, —SO$_2$CH$_3$, —CO$_2$R$^7$, —C(=O)NR$^7$R$^9$, —C(=O)R$^7$, or —CH$_2$—(CHOH)$_n$—CH$_2$OH;

each Het is independently, —NR$^7$, —NR$^{10}$, —S—, —SO—, or —SO$_2$—;

each g is, independently, an integer from 1 to 6;

each m is, independently, an integer from 1 to 7;

each n is, independently, an integer from 0 to 7;

each Q is, independently, C—R$^5$, C—R$^6$, or a nitrogen atom, wherein one, two or three Q in the ring are nitrogen atoms;

or a pharmaceutically acceptable salt thereof, and inclusive of all enantiomers, diastereomers, and racemic mixtures thereof.

2. The method of claim 1, wherein Y is —NH$_2$, X is Cl, each R$^2$, R$^1$, R$^3$, R$^L$ and R$^6$ is H, o is 4, p is 0 and x is a single bond.

3. The method of claim 2, wherein R$^5$ is
—(CH$_2$)$_n$—NR$^{12}$R$^{12}$,
—(CH$_2$)$_n$—N(SO$_2$R$^7$)$_2$,
—(CH$_2$)$_n$—N(R$^{11}$)$_2$,
—O—(CH$_2$)$_m$—NR$^{12}$R$^{12}$,
—O—(CH$_2$)$_m$—N(SO$_2$R$^7$)$_2$,
—O—(CH$_2$)$_m$—(Z)$_g$R$^{12}$,
—(CH$_2$)$_n$—CHNHBocCO$_2$R$^7$ (α)
—O—(CH$_2$)$_m$—CHNHBocCO$_2$R$^7$ (α),
—(CH$_2$)$_n$—N(R$^{11}$)$_2$,
—O—(CH$_2$)$_m$—N(R$^{11}$)$_2$,
—(CH$_2$)$_n$—CHNH$_2$CO$_2$R$_7$ (α),
—O—(CH$_2$)$_m$—CHNH$_2$CO$_2$R$^7$ (α),
—O—(CH$_2$)$_m$—N$^+$(R$^{11}$)$_3$,
—(CH$_2$)$_n$—(Z)$_g$—(CH$_2$)$_m$—NR$^{10}$R$^{10}$,
—C(=O)NH—(CH$_2$)$_m$—N(R$^{10}$)$_2$,
—NHC(=O)(CH$_2$)$_m$—N(R$^{10}$)$_2$,
—C(=O)NH—(CH$_2$)$_m$—NH—C(=NH)—NR$^7$)$_2$,
—NH—C(=O)—(CH$_2$)$_m$NH—C(=NH)—N(R$^{10}$)$_2$,
—O—(CH$_2$)$_m$—(CHOR$^8$)$_m$CH$_2$NR$^{10}$—(Z)$_g$—R$^{10}$,
—(CH$_2$)$_n$—(CHOR$^8$)$_m$CH$_2$—NR$^{10}$—(Z)$_g$—R$^{10}$,
—(CH$_2$)$_n$NR$^{10}$—(CH$_2$)$_m$(CHOR$^8$)$_n$CH$_2$NR$^{10}$—(Z)$_g$—R$^{10}$,
—O(CH$_2$)$_m$—NR$^{10}$—(CH$_2$)$_m$—(CHOH$^8$)$_n$CH$_2$NR$^{10}$—(Z)$_g$—R$^{10}$,
—(CH$_2$CH$_2$O)$_m$—CH$_2$CH$_2$NR$^{12}$R$^{12}$,
—O—(CH$_2$CH$_2$O)$_m$—CH$_2$CH$_2$NR$^{12}$R$^{12}$,
—(CH$_2$)$_n$—(C=O)NR$^{12}$R$^{12}$,
—O—(CH$_2$)$_m$—(C=O)NR$^{12}$R$^{12}$,
-(Het)-(CH$_2$)$_m$—OR$^8$,
-(Het)-(CH$_2$)$_m$—NR$^7$R$^{10}$,
-(Het)-(CH$_2$)$_m$CHOR$^8$)(CHOR$^8$)$_n$—CH$_2$OR$^8$,
-(Het)-(CH$_2$CH$_2$O)$_m$—R$^8$,
-(Het)-(CH$_2$CH$_2$O)$_m$—CH$_2$CH$_2$NR$^7$R$^{10}$,
-(Het)-(CH$_2$)$_m$—C(=O)NR$^7$R$^{10}$,
-(Het)-(CH$_2$)$_m$—(Z)$_g$—R$^7$,
-(Het)-(CH$_2$)$_m$—NR$^{10}$—CH$_2$(CHOR$^8$)(CHOR$^8$)$_n$—CH$_2$OR$^8$,
-(Het)-(CH$_2$)$_m$—CO$_2$R$^7$,
-(Het)-(CH$_2$)$_m$—NR$^{12}$R$^{12}$,
-(Het)-(CH$_2$)$_n$—NR$^{12}$R$^{12}$,
-(Het)-(CH$_2$)$_m$—(Z)$_g$R$^{12}$,
-(Het)-(CH$_2$)$_m$NR$^{11}$R$^{11}$,
-(Het)-(CH$_2$)$_m$—N$^⊕$—(R$^{11}$)$_3$,
-(Het)-(CH$_2$CH$_2$O)$_m$—CH$_2$CH$_2$NR$^{12}$R$^{12}$,
-(Het)-(CH$_2$)$_m$—(C=O)NR$^{12}$R$^{12}$,
-(Het)-(CH$_2$)$_m$—(CHOR$^8$)$_m$CH$_2$NR$^{10}$—(Z)$_g$—R$^{10}$,
-(Het)-(CH$_2$)$_m$—NR$^{10}$—(CH$_2$)$_m$—(CHOR$^8$)$_n$CH$_2$NR$^{10}$—(Z)$_g$—R$^{10}$,
—(CH$_2$)$_n$(CHOR$^8$)(CHOR$^8$)$_{1-7}$—CH$_2$OR$^8$, with the proviso that at least two —CH$_2$OR$^8$ are located 1,2- or 1,3- with respect to each other and the $R^8$ groups are joined to form a cyclic mono- or di-substituted 1,3-dioxane or 1,3-dioxolane,
—$(CH_2)_n$—$NR^{10}$—$CH_2(CHOR^8)(CHOR^8)_n$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane,
—O—$(CH_2)_m$—$NR^{10}$—$CH_2(CHOR^8)(CHOR^8)_n$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane, or
—O—$(CH_2)_m$—$NR^{10}$—$CH_2(CHOR^8)(CHOR^8)_{1-7}$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane.

4. The method of claim 1, wherein one Q in the ring is a nitrogen atom.

5. The method of claim 4, wherein Y is —$NH_2$, X is Cl, each $R^2$, $R^1$, $R^3$, $R^L$ and $R^6$ is H, o is 4, p is 0 and x is a single bond.

6. The method of claim 5, wherein $R^5$ is
—$(CH_2)_n$—$NR^{12}R^{12}$,
—$(CH_2)_n$—$N(SO_2R^7)_2$, —$(CH_2)_n$—$N(R^{11})_2$,
—O—$(CH_2)_m$—$NR^{12}R^{12}$,
—O—$(CH_2)_m$—$N(SO_2R^7)_2$,
—O—$(CH_2)_m$—$(Z)_gR^{12}$,
—$(CH_2)_n$—$CHNHBocCO_2R^7$ (α)
—O—$(CH_2)_m$—$CHNHBocCO_2R^7$ (α),
—$(CH_2)_n$—$N(R^{11})_2$,
—O—$(CH_2)_m$—$N(R^{11})_2$,
—$(CH_2)_n$—$CHNH_2CO_2R_7$ (α),
—O—$(CH_2)_m$—$CHNH_2CO_2R^7$ (α),
—O—$(CH_2)_m$—$N^+(R^{11})_3$,
—$(CH_2)_n$—$(Z)_g$—$(CH_2)_m$—$NR^{10}R^{10}$,
—C(=O)NH—$(CH_2)_m$—$N(R^{10})_2$,
—NHC(=O)$(CH_2)_m$—$N(R^{10})_2$,
—C(=O)NH—$(CH_2)_m$—NH—C(=NH)—$N(R^7)_2$,
—NH—C(=O)—$(CH_2)_m$NH—C(=NH)—$N(R^{10})_2$,
—O—$(CH_2)_m$—$(CHOR^8)_mCH_2NR^{10}$—$(Z)_g$—$R^{10}$,
—$(CH_2)_n$—$(CHOR^8)_mCH_2$—$NR^{10}$—$(Z)_g$—$R^{10}$,
—$(CH_2)_nNR^{10}$—$(CH_2)_m(CHOR^8)_nCH_2NR^{10}$—$(Z)_g$—$R^{10}$,
—O$(CH_2)_m$—$NR^{10}$—$(CH_2)_m(CHOH^8)_nCH_2NR^{10}$—$(Z)_g$—$R^{10}$,
—$(CH_2CH_2O)_m$—$CH_2CH_2NR^{12}R^{12}$,
—O—$(CH_2CH_2O)_m$—$CH_2CH_2NR^{12}R^{12}$,
—$(CH_2)_n$—(C=O)$NR^{12}R^{12}$,
—O—$(CH_2)_m$—(C=O)$NR^{12}R^{12}$,
-(Het)-$(CH_2)_m$—$OR^8$,
-(Het)-$(CH_2)_m$—$NR^7R^{10}$,
-(Het)-$(CH_2)_m(CHOR^8)(CHOR^8)_n$—$CH_2OR^8$,
-(Het)-$(CH_2CH_2O)_m$—$R^8$,
-(Het)-$(CH_2CH_2O)_m$—$CH_2CH_2NR^7R^{10}$,
-(Het)-$(CH_2)_m$—C(=O)$NR^7R^{10}$,
-(Het)-$(CH_2)_m$—$(Z)_g$—$R^7$,
-(Het)-$(CH_2)_m$—$NR^{10}$—$CH_2(CHOR^8)(CHOR^8)_n$—$CH_2OR^8$,
-(Het)-$(CH_2)_m$—$CO_2R^7$,
-(Het)-$(CH_2)_m$—$NR^{12}R^{12}$,
-(Het)-$(CH_2)_n$—$NR^{12}R^{12}$,
-(Het)-$(CH_2)_m$—$(Z)_gR^{12}$,
-(Het)-$(CH_2)_m NR^{11}R^{11}$,
-(Het)-$(CH_2)_m$—$N^\oplus$—$(R^{11})_3$,
-(Het)-$(CH_2CH_2O)_m$—$CH_2CH_2NR^{12}R^{12}$,
-(Het)-$(CH_2)_m$—(C=O)$NR^{12}R^{12}$,
-(Het)-$(CH_2)_m$—$(CHOR^8)_mCH_2NR^{10}$—$(Z)_g$—$R^{10}$,
-(Het)-$(CH_2)_m$—$NR^{10}$—$(CH_2)_m$—$(CHOR^8)_n$ $CH_2NR^{10}$—$(Z)_g$—$R^{10}$,
—$(CH_2)_n(CHOR^8)(CHOR^8)_{1-7}$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane,
—$(CH_2)_n$—$NR^{10}$—$CH_2(CHOR^8)(CHOR^8)_n$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane,
—O—$(CH_2)_m$—$NR^{10}$—$CH_2(CHOR^8)(CHOR^8)_n$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane, or
—O—$(CH_2)$, —$NR^{10}$—$CH_2(CHOR^8)(CHOR^8)_{1-7}$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane.

7. The method of claim 1, wherein two Q in the ring is a nitrogen atom.

8. The method of claim 7, wherein Y is —$NH_2$, X is Cl, each $R^2$, $R^1$, $R^3$, $R^L$ and $R^6$ is H, o is 4, p is 0 and x is a single bond.

9. The method of claim 8, wherein $R^5$ is
—$(CH_2)_n$—$NR^{12}R^{12}$,
—$(CH_2)_n$—$N(SO_2R^7)_2$,
—$(CH_2)_n$—$N(R^{11})_2$,
—O—$(CH_2)_m$—$NR^{12}R^{12}$, —O—$(CH_2)_m$—$N(SO_2R^7)_2$,
—O—$(CH_2)_m$—$(Z)_gR^{12}$,
—$(CH_2)_n$—$CHNHBocCO_2R^7$ (α)
—O—$(CH_2)_m$—$CHNHBocCO_2R^7$ (α),
—$(CH_2)_n$—$N(R^{11})_2$,
—O—$(CH_2)_m$—$N(R^{11})_2$,
—$(CH_2)_n$—$CHNH_2CO_2R_7$ (α),
—O—$(CH_2)_m$—$CHNH_2CO_2R^7$ (α), —O—$(CH_2)_m$—$N^+(R^{11})_3$,
—$(CH_2)_n$—$(Z)_g$—$(CH_2)_m$—$NR^{10}R^{10}$,
—C(=O)NH—$(CH_2)_m$—$N(R^{10})_2$,
—NHC(=O)$(CH_2)_m$—$N(R^{10})_2$,
—C(=O)NH—$(CH_2)_m$—NH—C(=NH)—$N(R^7)_2$,
—NH—C(=O)—$(CH_2)_m$NH—C(=NH)—$N(R^{10})_2$,
—O—$(CH_2)_m$—$(CHOR^8)_mCH_2NR^{10}$—$(Z)_g$—$R^{10}$,
—$(CH_2)_n$—$(CHOR^8)_mCH_2$—$NR^{10}$—$(Z)_g$—$R^{10}$,
—$(CH_2)_nNR^{10}$—$(CH_2)_m(CHOR^8)_nCH_2NR^{10}$—$(Z)_g$—$R^{10}$,
—O$(CH_2)_m$—$NR^{10}$—$(CH_2)_m$—$(CHOH^8)_nCH_2NR^{10}$—$(Z)_g$—$R^{10}$,
—$(CH_2CH_2O)_m$—$CH_2CH_2NR^{12}R^{12}$, —O—$(CH_2CH_2O)_m$—$CH_2CH_2NR^{12}R^{12}$,
—$(CH_2)_n$—(C=O)$NR^{12}R^{12}$,
—O—$(CH_2)_m$—(C=O)$NR^{12}R^{12}$,
-(Het)-$(CH_2)_m$—$OR^8$,
-(Het)-$(CH_2)_m$—$NR^7R^{10}$,
-(Het)-$(CH_2)_m(CHOR^8)(CHOR^8)_n$—$CH_2OR^8$,
-(Het)-$(CH_2CH_2O)_m$—$R^8$,
-(Het)-$(CH_2CH_2O)_m$—$CH_2CH_2NR^7R^{10}$,
-(Het)-$(CH_2)_m$—C(=O)$NR^7R^{10}$,
-(Het)-$(CH_2)_m$—$(Z)_g$—$R^7$,
-(Het)-$(CH_2)_m$—$NR^{10}$—$CH_2(CHOR^8)(CHOR^8)_n$—$CH_2OR^8$,
-(Het)-$(CH_2)_m$—$CO_2R^7$,
-(Het)-$(CH_2)_m$—$NR^{12}R^{12}$,
-(Het)-$(CH_2)_n$—$NR^{12}R^{12}$,
-(Het)-$(CH_2)_m$—$(Z)_gR^{12}$,
-(Het)-$(CH_2)_m NR^{11}R^{11}$,
-(Het)-$(CH_2)_m$—$N^\oplus$—$(R^{11})_3$, -(Het)-($CH_2CH_2O)_m$—$CH_2CH_2NR^{12}R^{12}$,
-(Het)-($CH_2)_m$—(C=O)$NR^{12}R^{12}$,
-(Het)-($CH_2)_m$—($CHOR^8)_m CH_2NR^{10}$—$(Z)_g$—$R^{10}$,
-(Het)-($CH_2)_m$—$NR^{10}$—($CH_2)_m$—($CHOR^8)_n$ $CH_2NR^{10}$—$(Z)_g$—$R^{10}$,
—($CH_2)_n(CHOR^8)(CHOR^8)_{1-7}$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane,
—($CH_2)_n$—$N^{10}$—$CH_2(CHOR^8)(CHOR^8)_n$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane,
—O—($CH_2)_m$—$NR^{10}$—$CH_2(CHOR^8)(CHOR^8)_n$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane, or
—O—($CH_2)_m$—$NR^{10}$—$CH_2(CHOR^8)(CHOR^8)_{1-7}$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane.

10. The method of claim 1, wherein three Q in the ring is a nitrogen atom.

11. The method of claim 10, wherein Y is —$NH_2$, X is Cl, each $R^2$, $R^1$, $R^3$, $R^L$ and $R^6$ is H, o is 4, p is 0 and x is a single bond.

12. The method of claim 11, wherein $R^5$ is
—($CH_2)_n$—$NR^{12}R^{12}$,
—($CH_2)_n$—$N(SO_2R^7)_2$,
—($CH_2)_n$—$N(R^{11})_2$,
—O—($CH_2)_m$—$NR^{12}R^{12}$,
—O—($CH_2)_m$—$N(SO_2R)_2$,
—O—($CH_2)_m$—$(Z)_g R^{12}$,
—($CH_2)_n$—$CHNHBocCO_2R^7$ (α)
—O—($CH_2)_m$—$CHNHBocCO_2R^7$ (α), —($CH_2)_n$—$N(R^{11})_2$,
—O—($CH_2)_m$—$N(R^{11})_2$,
—($CH_2)_n$—$CHNH_2CO_2R_7$ (α),
—O—($CH_2)_m$—$CHNH_2CO_2R^7$ (α),
—O—($CH_2)_m$—$N^+(R^{11})_3$,
—($CH_2)_n$—$(Z)_g$—($CH_2)_m$—$NR^{10}R^{10}$,
—C(=O)NH—($CH_2)_m$—$N(R^{10})_2$,
—NHC(=O)($CH_2)_m$—$N(R^{10})_2$,
—C(=O)NH—($CH_2)_m$—NH—C(=NH)—$N(R^7)_2$,
—NH—C(=O)—($CH_2)_m$NH—C(=NH)—$N(R^{10})_2$,
—O—($CH_2)_m$—($CHOR^8)_m CH_2NR^{10}$—$(Z)_g$—$R^{10}$,
—($CH_2)_n$—($CHOR^8)_m CH_2$—$NR^{10}$—$(Z)_g$—$R^{10}$,
—($CH_2)_n NR^{10}$—($CH_2)_m(CHOR^8)_n CH_2NR^{10}$—$(Z)_g$—$R^{10}$,
—O($CH_2)_m$—$NR^{10}$—($CH_2)_m$—$(CHOH^8)_n CH_2NR^{10}$—$(Z)_g$—$R^{10}$,
—($CH_2CH_2O)_m$—$CH_2CH_2NR^{12}R^{12}$,
—O—($CH_2CH_2O)_m$—$CH_2CH_2NR^{12}R^{12}$,
—($CH_2)_n$—(C=O)$NR^{12}R^{12}$,
—O—($CH_2)_m$—(C=O)$NR^{12}R^{12}$,
-(Het)-($CH_2)_m$—$OR^8$,
-(Het)-($CH_2)_m$—$NR^7R^{10}$,
-(Het)-($CH_2)_m(CHOR^8)(CHOR^8)_n CH_2OR^8$,
-(Het)-($CH_2CH_2O)_m$—$R^8$,
-(Het)-($CH_2CH_2O)_m$—$CH_2CH_2NR^7R^{10}$,
-(Het)-($CH_2)_m$—C(=O)$NR^7R^{10}$,
-(Het)-($CH_2)_m$—$(Z)_g$—$R^7$,
-(Het)-($CH_2)_m$—$NR^{10}$—$CH_2(CHOR^8)(CHOR^8)_n$—$CH_2OR^8$,
-(Het)-($CH_2)_m$—$CO_2R^7$,
-(Het)-($CH_2)_m$—$NR^{12}R^{12}$,
-(Het)-($CH_2)_n$—$NR^{12}R^{12}$,
-(Het)-($CH_2)_m$—$(Z)_g R^{12}$,
-(Het)-($CH_2)_m NR^{11}R^{11}$,
-(Het)-($CH_2)_m$—$N^\oplus$—$(R^{11})_3$,
-(Het)-($CH_2CH_2O)_m$—$CH_2CH_2NR^{12}R^{12}$,
-(Het)-($CH_2)_m$—(C=O)$NR^{12}R^{12}$,
-(Het)-($CH_2)_m$—($CHOR^8)_m CH_2NR^{10}$—$(Z)_g$—$R^{10}$,
-(Het)-($CH_2)_m$—$NR^{10}$—($CH_2)_m$—$(CHOR^8)_n$ $CH_2NR^{10}$—$(Z)_g$—$R^{10}$,
—($CH_2)_n(CHOR^8)(CHOR^8)_{1-7}$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane,
—($CH_2)_n$—$NR^{10}$—$CH_2(CHOR^8)(CHOR^8)_n$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane,
—O—($CH_2)_m$—$NR^{10}$—$CH_2(CHOR^8)(CHOR^8)_n$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane, or
—O—($CH_2)_m$—$NR^{10}$—$CH_2(CHOR^8)(CHOR^8)_{1-7}$—$CH_2OR^8$, with the proviso that at least two —$CH_2OR^8$ are located 1,2- or 1,3- with respect to each other and the $R^8$ groups are joined to form a cyclic mono- or di-substituted 1,3-dioxane or 1,3-dioxolane.

\* \* \* \* \*